(12) United States Patent
Ziv et al.

(10) Patent No.: US 11,376,155 B2
(45) Date of Patent: Jul. 5, 2022

(54) DEVICES AND METHODS FOR PELVIC ORGAN PROLAPSE ALLEVIATION

(71) Applicant: ConTIPI Medical Ltd., Caesarea (IL)

(72) Inventors: Elan Ziv, Ramat-Gan (IL); Zohar Tyroler, Hod-HaSharon (IL); Elisheva Fabrikant, Herzlia (IL); Tal Caspi, Pardes Chana—Karkur (IL)

(73) Assignee: ConTIPI Medical Ltd., Caesarea (IL)

( * ) Notice: Subject to any disclaimer, the term of this patent is extended or adjusted under 35 U.S.C. 154(b) by 1032 days.

(21) Appl. No.: 14/881,200

(22) Filed: Oct. 13, 2015

(65) Prior Publication Data

US 2017/0100278 A1    Apr. 13, 2017

(51) Int. Cl.
*A61F 6/12* (2006.01)

(52) U.S. Cl.
CPC .................... *A61F 6/12* (2013.01)

(58) Field of Classification Search
CPC ........ A61F 6/00; A61F 6/06; A61F 6/08–202; A61F 2/00–005; A61B 17/12; A61B 17/12022–12045; A61B 17/12099–12154; A61B 17/12172; A61K 9/0012; A61K 9/0034–0039
See application file for complete search history.

(56) References Cited

U.S. PATENT DOCUMENTS

| | | |
|---|---|---|
| 7,050 A | 1/1850 | Caulkins et al. |
| 80,163 A | 7/1868 | Gorgas et al. |
| 1,334,237 A | 3/1920 | Fleck |
| 2,201,274 A | 5/1940 | Singer |
| 2,398,518 A * | 4/1946 | Clark ............... A61F 6/146 128/841 |
| 3,811,423 A | 5/1974 | Dickinson, III et al. |
| 4,246,896 A | 1/1981 | Horne, Jr. et al. |
| 4,307,716 A | 12/1981 | Davis |

(Continued)

FOREIGN PATENT DOCUMENTS

| | | |
|---|---|---|
| CN | 2464263 | 12/2001 |
| CN | 101287422 | 10/2008 |

(Continued)

OTHER PUBLICATIONS

International Search Report and the Written Opinion Dated Apr. 20, 2017 From the International Searching Authority Re. Application No. PCT/IL2016/051112. (15 Pages).

(Continued)

*Primary Examiner* — Michelle J Lee

(57) ABSTRACT

A device sized and shaped for alleviating organ prolapse when inserted into a vagina, comprising: (a) an adjustably flexible, substantially planar ring; (b) a telescoping locking mechanism extending in a central axis, but within the plane of the ring, from a first side of the ring to a second side of the ring, comprising, (i) a first element extending from a side of the ring including an elastic diamond shaped snap, and, (ii) a second element extending from a second side of the ring, opposite the first element, including at least one window configured as a counterpart to the snap, wherein the device is configured to be in an expanded, treatment rendering state when the snap is released into the window and a reduced profile state when the snap is not in the window.

14 Claims, 44 Drawing Sheets

(56) References Cited

U.S. PATENT DOCUMENTS

| | | | |
|---|---|---|---|
| 4,620,534 | A | 11/1986 | Zartman |
| 4,677,967 | A | 7/1987 | Zartman |
| 4,823,814 | A | 4/1989 | Drogendijk et al. |
| 5,014,722 | A * | 5/1991 | Bauer ............... A61F 6/142 128/830 |
| 5,224,494 | A | 7/1993 | Enhorning |
| 5,355,896 | A | 10/1994 | Schulman |
| 5,632,756 | A | 5/1997 | Kruglick |
| 5,771,899 | A | 6/1998 | Martelly et al. |
| 5,894,842 | A | 4/1999 | Rabin et al. |
| 6,158,435 | A | 12/2000 | Dorsey |
| 6,216,698 | B1 | 4/2001 | Regula |
| 6,503,190 | B1 | 1/2003 | Ulmsten et al. |
| 6,645,137 | B2 | 11/2003 | Ulmsten et al. |
| 6,808,485 | B2 | 10/2004 | Zunker |
| 6,982,515 | B2 | 1/2006 | Howell et al. |
| 7,036,511 | B2 | 5/2006 | Nissenkorn |
| 8,302,608 | B2 | 11/2012 | Harmani |
| 8,573,221 | B2 | 11/2013 | Sakhel |
| 8,651,109 | B2 | 2/2014 | Ziv et al. |
| 8,728,013 | B2 | 5/2014 | Perle et al. |
| 10,507,094 | B2 | 12/2019 | Harmanli |
| 2003/0149334 | A1 | 8/2003 | Ulmsten et al. |
| 2008/0009931 | A1 | 1/2008 | Bartning et al. |
| 2008/0167599 | A1 | 7/2008 | Osborn et al. |
| 2008/0281149 | A1 | 11/2008 | Sinai et al. |
| 2009/0171139 | A1 | 7/2009 | Chu |
| 2009/0203959 | A1 | 8/2009 | Ziv et al. |
| 2009/0266367 | A1 * | 10/2009 | Ziv ........................ A61F 6/08 128/834 |
| 2009/0283009 | A1 | 11/2009 | Bravo et al. |
| 2009/0283099 | A1 | 11/2009 | Harmanli |
| 2010/0286791 | A1 * | 11/2010 | Goldsmith ......... A61B 17/0057 623/23.7 |
| 2013/0025604 | A1 | 1/2013 | Harmanli |
| 2013/0053863 | A1 | 2/2013 | Juravic et al. |
| 2013/0324381 | A1 | 12/2013 | Horsley |
| 2013/0327338 | A1 | 12/2013 | Churchill et al. |
| 2014/0073846 | A1 | 3/2014 | Sinai et al. |
| 2014/0100416 | A1 | 4/2014 | Durling et al. |
| 2014/0158138 | A1 | 6/2014 | Ziv et al. |
| 2014/0261445 | A1 | 9/2014 | Maaskamp et al. |
| 2014/0275744 | A1 | 9/2014 | Rosen et al. |
| 2015/0133725 | A1 | 5/2015 | Ziv et al. |
| 2016/0015500 | A1 | 1/2016 | Ziv et al. |

FOREIGN PATENT DOCUMENTS

| | | |
|---|---|---|
| CN | 101511302 | 8/2009 |
| CN | 102083389 | 6/2011 |
| CN | 202313882 | 7/2012 |
| CN | 102753124 | 10/2012 |
| DE | 169862 | 7/1905 |
| EP | 2276419 | 11/2011 |
| FR | 2843700 | 2/2004 |
| GB | 235218 | 10/1925 |
| GB | 1115727 | 5/1968 |
| JP | 06-133996 | 5/1994 |
| WO | WO 96/01084 | 1/1996 |
| WO | WO 03/047476 | 6/2003 |
| WO | WO 2004/103213 | 12/2004 |
| WO | WO 2008/079271 | 7/2008 |
| WO | WO 2009/130702 | 10/2009 |
| WO | WO 2014/127270 | 8/2014 |
| WO | WO 2014/127295 | 8/2014 |
| WO | WO 2017/064712 | 4/2017 |
| WO | WO 2017/064713 | 4/2017 |
| WO | WO 2017/064714 | 4/2017 |

OTHER PUBLICATIONS

International Search Report and the Written Opinion Dated Mar. 2, 2017 From the International Searching Authority Re. Application No. PCT/IL2016/051114. (12 Pages).

International Search Report and the Written Opinion Dated Mar. 3, 2017 From the International Searching Authority Re. Application No. PCT/IL2016/051113. (13 Pages).

Invitation to Pay Additional Fees Dated Feb. 2, 2017 From the International Searching Authority Re. Application No. PCT/IL2016/051112. (2 Pages).

International Preliminary Report on Patentability Dated Apr. 26, 2018 From the International Bureau of WIPO Re. Application No. PCT/IL2016/051112. (9 Pages).

International Preliminary Report on Patentability Dated Apr. 26, 2018 From the International Bureau of WIPO Re. Application No. PCT/IL2016/051113. (8 Pages).

International Preliminary Report on Patentability Dated Apr. 26, 2018 From the International Bureau of WIPO Re. Application No. PCT/IL2016/051114. (8 Pages).

Supplementary European Search Report and the European Search Opinion Dated Jun. 24, 2019 From the European Patent Office Re. Application No. 16855065.5. (8 Pages).

Supplementary European Search Report and the European Search Opinion Dated Jun. 24, 2019 From the European Patent Office Re. Application No. 16855064.8. (9 Pages).

Supplementary Partial European Search Report and the European Search Opinion Dated Sep. 9, 2019 From the European Patent Office Re. Application No. 16855066.3. (10 Pages).

Notification of Office Action and Search Report Dated Jun. 11, 2020 From the State Intellectual Property Office of the People's Republic of China Re. Application No. 201680072760.0. (8 Pages).

Notification of Office Action and Search Report Dated Apr. 16, 2020 From the State Intellectual Property Office of the People's Republic of China Re. Application No. 201680072759.8. (7 Pages).

Notification of Office Action Dated Apr. 20, 2020 From the State Intellectual Property Office of the People's Republic of China Re. Application No. 201680072943.2. (4 Pages).

Official Action Dated Jun. 11, 2020 from the US Patent and Trademark Office Re. U.S. Appl. No. 15/767,390. (29 pages).

Search Report and Explanationd Dated Jun. 9, 2020 From the Servico Publico Federal, Ministerio da Economia, Institute Nacional da Propriedade Industrial do Brasil Re. BR112018007546-9 and Its Summary in English. (5 Pages).

Search Report and Explanationd Dated Jun. 9, 2020 From the Servico Publico Federal, Ministerio da Economia, Institute Nacional da Propriedade Industrial do Brasil Re. BR112018007548-5 and Its Summary in English. (5 Pages).

Search Report and Explanations Dated Jun. 9, 2020 From the Servico Publico Federal, Ministerio da Economia, Institute Nacional da Propriedade Industrial do Brasil Re. Application No. BR112018007542-6 and Its Summary in English. (5 Pages).

Summary Dated May 12, 2020 of Notification of Office Action Dated Apr. 16, 2020 From the State Intellectual Property Office of the People's Republic of China Re. Application No. 201680072759.8. (2 Pages).

Summary Dated May 13, 2020 of Notification of Office Action Dated Apr. 20, 2020 From the State Intellectual Property Office of the People's Republic of China Re. Application No. 201680072943.2. (2 Pages).

Official Action Dated Sep. 17, 2020 from the US Patent and Trademark Office Re. U.S. Appl. No. 15/767,401. (33 pages).

Communication Pursuant to Article 94(3) EPC Dated May 10, 2021 From the European Patent Office Re. Application No. 16855065.5. (5 Pages).

Decision of Rejection Dated May 18, 2021 From the State Intellectual Property Office of the People's Republic of China Re. Application No. 201680072760.0. (5 Pages).

Examination Report Under Sections 12 & 13 of the Patents Act, 1970 and the Patents Rules, 2003 Dated May 24, 2021 From the Government of India, Intellectual Property India, Patents, Designs,

(56) References Cited

OTHER PUBLICATIONS

Trade Marks, Geographical Indications, The Patent Office Re. Application No. 201837017313. (5 Pages).
Final Official Action Dated May 28, 2021 from the US Patent and Trademark Office Re. U.S. Appl. No. 15/767,401. (20 pages).
Notification of Decision of Rejection Dated Mar. 11, 2021 From the State Intellectual Property Office of the People's Republic of China Re. Application No. 201680072943.2. (6 Pages).
Translation Dated Jun. 8, 2021 of Notification of Decision of Rejection Dated Mar. 11, 2021 From the State Intellectual Property Office of the People's Republic of China Re. Application No. 201680072943.2. (10 Pages).
Notification of Office Action Dated Dec. 25, 2020 From the State Intellectual Property Office of the People's Republic of China Re. Application No. 201680072760.0. and its English Summary (8 Pages).
Official Action Dated Jan. 29, 2021 From the US Patent and Trademark Office Re. U.S. Appl. No. 15/767,390. (23 Pages).
English Summary Dated Aug. 12, 2021 of Notification of Office Action Dated May 18, 2021 From the State Intellectual Property Office of the People's Republic of China Re. Application No. 201680072760.0. (2 Pages).
Examination Report Under Sections 12 & 13 of the Patents Act, 1977 and the Patents Rules, 2003 Dated Jun. 5, 2021 From the Government of India, Intellectual Property India, Patents, Designs, Trade Marks, Geographical Indications, The Patent Office Re. Application No. 201837017323. (6 Pages).
Final Official Action Dated Aug. 4, 2021 from the US Patent and Trademark Office Re. Application No. 15/767,390. (24 pages).
Under Sections 12 & 13 of the Patents Act, 1970 and the Patents Rules, 2003 Dated Jun. 5, 2021 From the Government of India, Intellectual Property India, Patents, Designs, Trade Marks, Geographical Indications, The Patent Office Re. Application No. 201837017341. (7 Pages).
Dictonary "Dictionary Definitions Circumference", 2021.
Notice of Allowance Dated Jan. 26, 2022 together with Interview Summary Dated Dec. 1, 2021from US Patent and Trademark Office Re. U.S. Appl. No. 15/767,390. (15 pages).
Communication Pursuant to Article 94(3) EPC Dated Sep. 15, 2021 From the European Patent Office Re. Application No. 16855065.5. (4 Pages).
Notification of Office Action and Search Report Dated Oct. 24, 2019 From the State Intellectual Property Office of the People's Republic of China Re. Application No. 201680072943.2. (9 Pages).
Translation of Notification Dated Nov. 17, 2019 From OA of People's Republic of China Re. Application No. 201680072943.2. (9 Pages).

\* cited by examiner

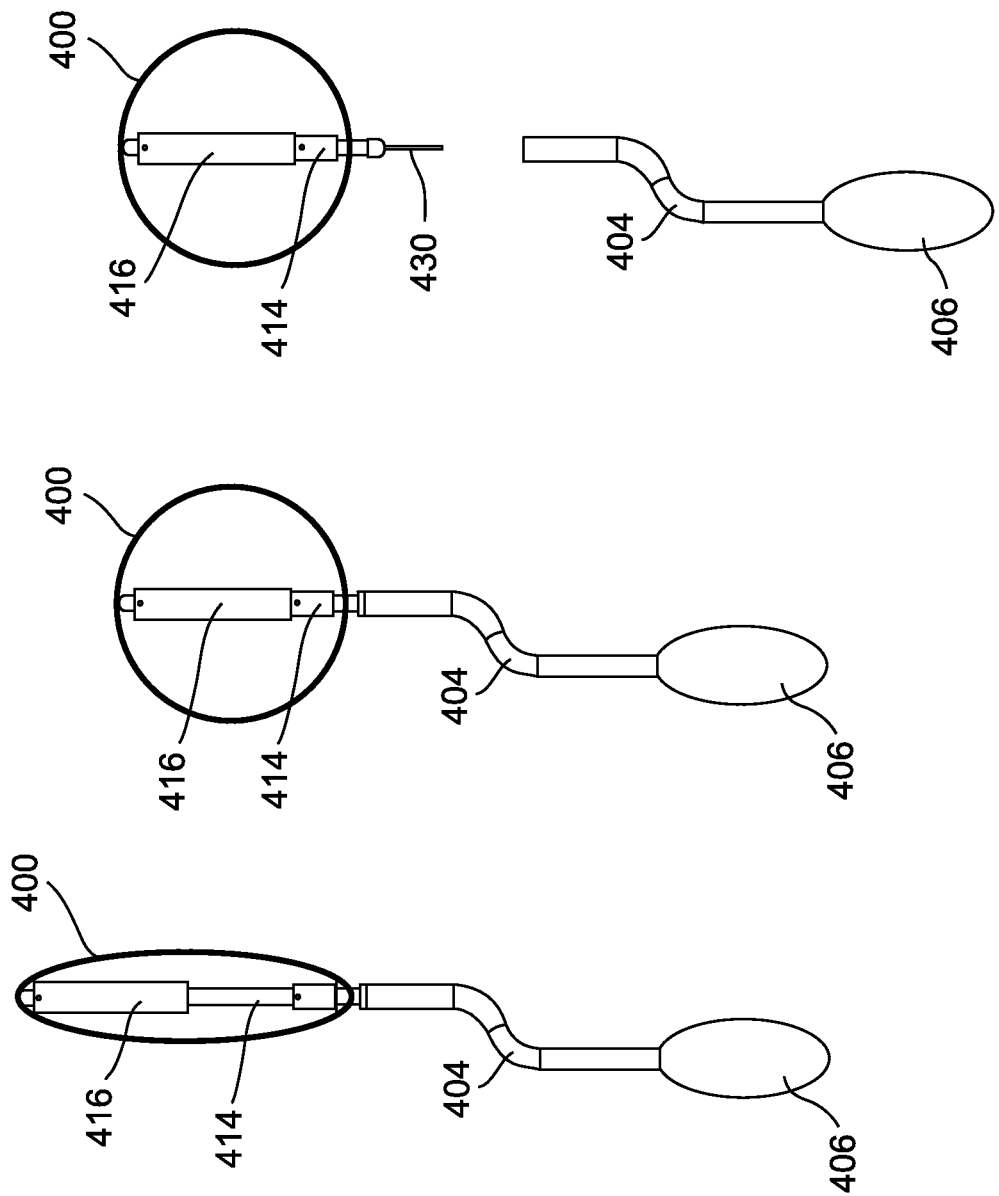

DEVICES AND METHODS FOR PELVIC ORGAN PROLAPSE ALLEVIATION

FIELD AND BACKGROUND OF THE INVENTION

The present invention, in some embodiments thereof, relates to the health care industry and, more particularly, but not exclusively, to devices and methods for treating feminine pelvic organ prolapse.

Pelvic organ prolapse occurs when the network of muscles, ligaments, and tissues that hold the pelvic organs in place is weakened and one or more pelvic organs descend into the vaginal cavity. Pelvic organ prolapse occurs as a result of normal aging, childbirth, pelvic surgery or trauma, and may include one or more of the following conditions:

i) Cystocele, the leading form of pelvic organ prolapse, wherein the bladder drops into the vagina and may be associated with urination problems;

ii) Rectocele, wherein the rectum herniates into the vagina and may result in difficulty and/or pain with defecation;

iii) Enterocele, wherein the small intestine prolapses into the vagina;

iv) Uterine prolapse wherein the uterus drops downward into the vagina and is often associated other organ prolapse; and v) Vaginal vault prolapse, wherein the top portion of the vagina, the apex, loses its natural shape and drops down into the lower vaginal canal, and may occur in women who had a hysterectomy.

To avoid surgical procedures to treat pelvic organ prolapse, a number of non-surgical vaginal devices, pessaries, have been designed to be inserted into the vagina by a surgeon, medical assistant or user.

Background art includes the following patents, the contents of all of which are incorporated by reference as if fully set forth herein:
WO 2009/130702: Pessaries for Prolapse Alleviation;
U.S. Pat. No. 8,651,109: Pessaries for Prolapse Alleviation;
WO 9601084: Inflatable Vaginal Pessary;
GB 235218: Inflatable Pessary;
FR 2843700: Rehabilitation Device for Urinary and Faecal Continence;
WO 03047476: Vaginal Pessary;
GB 1115727: Apparatus Controlling Incontinence in the Female;
U.S. Pat. No. 5,224,494: Vaginal Pessary;
U.S. Pat. No. 6,158,435: Pessary;
US 2003149334: Vaginal Pessary;
JP 6133996: Pessary for Treating Prolapse of Uterus;
U.S. Pat. No. 4,823,814: Pessary;
U.S. Pat. No. 5,771,899: Pessary;
U.S. Pat. No. 5,894,842: Pessary for Treating Vaginal Prolapse;
U.S. Pat. No. 6,158,435: Pessary;
U.S. Pat. No. 6,216,698: Flexible Pessary;
U.S. Pat. No. 6,503,190: Vaginal Pessary;
U.S. Pat. No. 6,808,485: Compressible Resilient Vaginal Incontinence Insert; and
U.S. Pat. No. 7,036,511: Vaginal Pessary.

SUMMARY OF THE INVENTION

There is provided in accordance with an exemplary embodiment of the invention, a device sized and shaped for alleviating organ prolapse when inserted into a vagina, comprising: (a) an adjustably flexible, substantially planar ring; (b) a telescoping locking mechanism extending in a central axis, but within the plane of the ring, from a first side of the ring to a second side of the ring, comprising, (i) a first element extending from a side of the ring including an elastic diamond shaped snap, and, (ii) a second element extending from a second side of the ring, opposite the first element, including at least one window configured as a counterpart to the snap, wherein the first element is configured to slide axially within the second element such that when the snap is opposite the window, the snap is released into the window reversibly preventing further axial movement of the first element relative to the second element and wherein the device is configured to be in an expanded, treatment rendering state when the snap is released into the window and a reduced profile state when the snap is not in the window.

In an embodiment of the invention, the device further comprises a padded cover around at least a portion of the ring.

In an embodiment of the invention, the device further comprises a removal string attached to the first element and configured to contract the diamond shaped snapping element towards the central axis of the ring, removing the snap from the window, upon the application of a proximal force on the removal string.

In an embodiment of the invention, the ring is substantially rigid in the locked, expanded state and where the ring is flexible when not in the expanded state.

In an embodiment of the invention, the elastic diamond shaped snap comprises at least two opposing prongs and the second element is configured with two counterpart windows for the prongs.

In an embodiment of the invention, the ring is discontinuous, connected by the cover.

In an embodiment of the invention, the device is configured to be bi-stable, stable in both the expanded state and the reduced profile state.

In an embodiment of the invention, the locking mechanism is configured to extend sufficiently from one side of the ring to another side of the ring to inhibit organ prolapse through the center of the ring.

In an embodiment of the invention, the device further comprises an applicator configured to insert into and deploy the device in a vagina, comprising, (a) a holder with at least two grooves configured to hold the device where the grooves are penetrated by two counterpart mounds on the device; and, (b) a pusher configured to move axially within the holder and to press the device being held in the holder from the reduced profile state into the expanded state, and to push wings of the applicator aside in order to disengage device.

In an embodiment of the invention, the holder is provided with diagonal walls which slope up moving towards the second side of the device and where the pusher is configured with two protruding arms with sloped edges which force the holder open to release the grooves of the holder from the mounds of the device as the pusher is pushed in a distal direction and the sloped edges of the arms force against the diagonal walls of the holder.

In an embodiment of the invention, the holder and pusher are configured to force the holder open distally of where the device is pressed into the expanded state by the pusher.

In an embodiment of the invention, the holder is configured with a gripping area to facilitate the grip of the applicator by the user and where the gripping area is configured with a soft grip for enhanced user comfort.

In an embodiment of the invention, the gripping area is positioned to ensure proper depth of insertion.

In an embodiment of the invention, the applicator further comprises a locking mechanism which locks the pusher into the holder.

There is further provided in accordance with an exemplary embodiment of the invention, a device sized and shaped for alleviating organ prolapse when inserted into a vagina, comprising: (a) an adjustably flexible, substantially planar ring; (b) a locking mechanism located along a central axis of the ring, but within the plane of the ring, comprising, (i) an inner tube or piston extending from the first side of the ring toward the second side of the ring, and, (ii) an external tube extending from the second side of the ring towards the first side of the ring and the inner tube, wherein the inner tube is configured to fit within the external tube and slide at least partially within the external tube and reversibly lock the inner tube and external tube together to prevent additional relative movement between the tubes and wherein the device is configured to be in an expanded, treatment rendering state when the tubes are reversibly locked to each other and a reduced profile state when the tubes are unlocked.

In an embodiment of the invention, the inner tube includes an elastic diamond shaped snapping element and the external tube includes at least one counterpart window configured to receive the snapping element to reversibly lock the device.

In an embodiment of the invention, the inner tube includes snapping elements located near the second end of the inner tube and the external tube includes counterpart internal grooves or windows configured to receive the snapping elements to reversibly lock the device.

In an embodiment of the invention, the device is configured to slide the inner tube within the external tube using pneumatic pressure.

In an embodiment of the invention, the device is configured to slide the inner tube within the external tube using mechanical pressure.

In an embodiment of the invention, the device further comprises a padded elastic cover around at least a portion of the ring.

In an embodiment of the invention, the device further comprises a removal string configured to unlock the locking mechanism upon the application of a proximal force on the removal string.

In an embodiment of the invention, the ring is substantially rigid in the locked, expanded state and where the ring is flexible when not in the expanded state.

In an embodiment of the invention, the device further comprises an applicator configured to insert into and deploy the device in a vagina, comprising, (a) a holder configured to hold the device, and, (b) a pusher configured to move axially within the holder and to transition the device being held in the holder from the reduced profile state into the expanded state.

In an embodiment of the invention, the applicator is configured to transition the device by pulling the pusher proximally inside the holder until the device reversibly locks in the expanded state.

In an embodiment of the invention, the applicator is configured to transition the device by pushing the pusher distally inside the holder until the device reversibly locks in the expanded state.

In an embodiment of the invention, the device further comprises a pump configured to actuate a piston, using pneumatic pressure, to slide in a distal direction in an external tube to reversibly transition the device from the reduced profile state to the expanded state.

In an embodiment of the invention, the device further comprises an inlet tube operatively connecting the pump to the piston.

In an embodiment of the invention, the inlet tube is configured to release the pressure in the piston upon an application of a proximal force or the opening of a valve, thereby transitioning the device from the expanded state to the reduced profile state.

In an embodiment of the invention, the device further comprises a removal string configured to transition the device from the expanded state to the reduced profile state by pulling at least one snapping element towards a central axis of the device, releasing the piston.

In an embodiment of the invention, the cover is continuous but the ring is not.

There is further provided in accordance with an exemplary embodiment of the invention, a locking mechanism for releasably locking a prolapse alleviating device in an expanded state, comprising: a first component configured with at least one snapping element; and, a second component configured with a counterpart for receipt of the snapping element therein; and, a removal string for releasing the second component from the first component, wherein when the first component is received in the second component, relative movement between the first and second components is disabled and when the removal string releases the components from each other, relative movement is re-enabled.

In an embodiment of the invention, the at least one snapping element is located at a second end, and is an integral part, of the first component and the second component is configured with at least one cut out for receipt of the snapping element.

In an embodiment of the invention, the locking mechanism further comprises a bridge connected to the snapping element and the removal string and configured to contract the snapping element when force in a proximal direction is applied to the bridge through the removal string.

In an embodiment of the invention, the snapping element is the top of the first component and the second component comprises two flexible arms, each configured with a trans-axial groove, the two trans-axial grooves adapted to receive together the top of the first component.

In an embodiment of the invention, the locking mechanism further comprises an opening element configured to release the first component from the second component by sliding in a proximal direction within an axial groove provided to each of the flexible arms upon the application of a force in a proximal direction on the opening element by the removal string.

In an embodiment of the invention, the snapping element is comprised of two halves which rotate about a common axis and the second component includes counterpart cut outs within which the snapping element snaps.

In an embodiment of the invention, the locking mechanism further comprises a holder configured to hold at least a part of each of the halves and connected to the removal string such that a proximal force on the removal string detaches the holder from the two halves, freeing the halves to rotate the snapping element out of the cut outs.

There is further provided in accordance with an exemplary embodiment of the invention, an applicator for at least one of inserting, expanding and deploying a prolapse alleviating device, comprising: a holder configured for holding the prolapse alleviating device, and, a pusher coaxially located within the holder and configured to slide with respect to the holder to exert pressure on the device in the holder for expanding and deploying the device.

In an embodiment of the invention, the pusher has a channel therethrough for a removal string.

In an embodiment of the invention, the applicator further comprises a protruding snap element configured to mate with a slot in the device to prevent the device from detaching from the holder.

In an embodiment of the invention, the holder has two reversibly connected arms configured with nesting retaining elements which retain the device in the holder and against which the device is held while the pusher exerts pressure on the device to expand it.

In an embodiment of the invention, the applicator further comprises a trapping element located at a distal end of arms of the holder and configured to reversibly connect, and to trap the device within, the arms.

In an embodiment of the invention, the applicator further comprises a protruding snap element located at a distal end of arms of the holder and configured to reversibly connect, and to trap the device within, the arms.

In an embodiment of the invention, the applicator further comprises at least one protruding concentric pillar located at a distal end of arms of the holder and configured to reversibly connect, and to trap the device within, the arms.

In an embodiment of the invention, the applicator further comprises a band located at a distal end of, and around, arms of the holder and configured to reversibly connect, and to trap the device within, the arms.

In an embodiment of the invention, the band is attached to one of the arms.

In an embodiment of the invention, the applicator is configured with holes which are counterparts to pins on the device where the device is maintained in the applicator when the pins are inserted into the holes.

In an embodiment of the invention, the arms of the pusher are configured to slide within rails on the holder.

In an embodiment of the invention, the rails on the holder are configured with a releasing part which is located on the rails at a length sufficient to maintain the holder closed as the pusher arms travel within the rails but release the holder after the pusher is finished with expanding the device.

There is further provided in accordance with an exemplary embodiment of the invention, a reversibly lockable device for treating pelvic organ prolapse, comprising: a plurality of sections connected by hinges, where the sections are shaped and configured to form a circular shape when the device is in an expanded state; a plurality of cuts within each of the plurality of sections configured to receive at least one of an applicator arm and a spring lock; and, at least one spring lock located in a cut on a first section opposite a cut on an opposing section and adapted to pop into the cut on the opposing section when the cuts are aligned.

In an embodiment of the invention, the device further comprises an elastomeric cap.

In an embodiment of the invention, the device further comprises an applicator provided with applicator arms configured for insertion into the cuts in the sections of the device.

In an embodiment of the invention, the applicator is configured to transition the device from a compressed state to the expanded state by rotating the applicator arms located in the cuts of the device.

In an embodiment of the invention, the device further comprises a removal string attached to the at least one spring lock and configured to remove the spring lock from the cut on the opposing section upon the application of a force in the proximal direction.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example, and not necessarily to scale, and are for purposes of illustrative discussion of embodiments of the invention. In this regard, the description taken with the drawings makes apparent to those skilled in the art how embodiments of the invention may be practiced.

In the drawings:

FIGS. 12A-12C are front views of a device with an internal piston with a pressure valve connected by a detachable tube to an inflator, in accordance with an exemplary embodiment of the invention;

DESCRIPTION OF SPECIFIC EMBODIMENTS OF THE INVENTION

Figure 1:
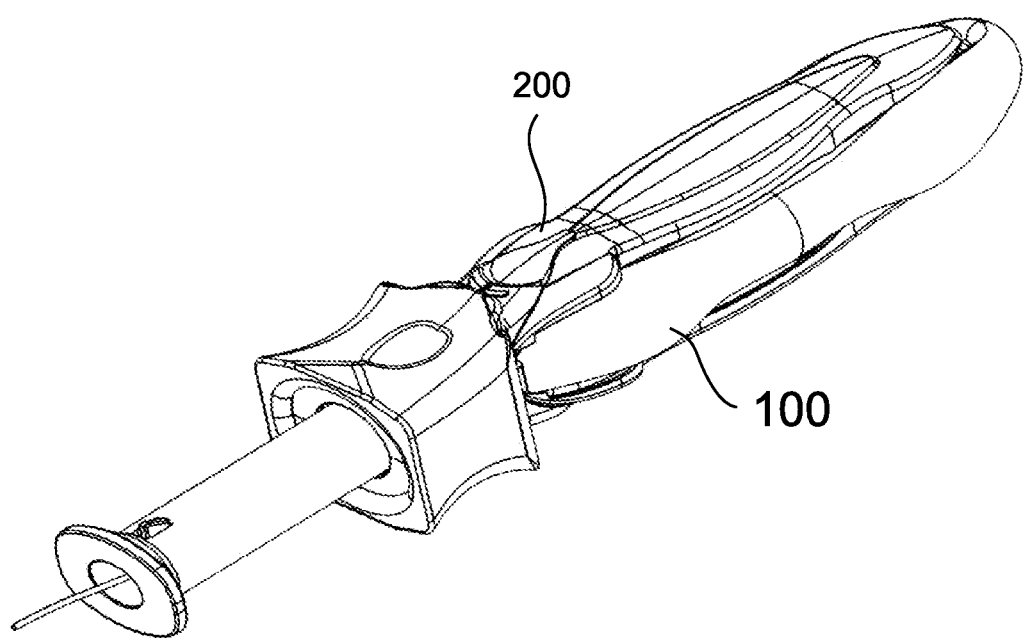
FIG. 1 is a perspective view of prolapse treating device with snapping elements attached to an applicator, in accordance with an exemplary embodiment of the invention.
Figure 2A:
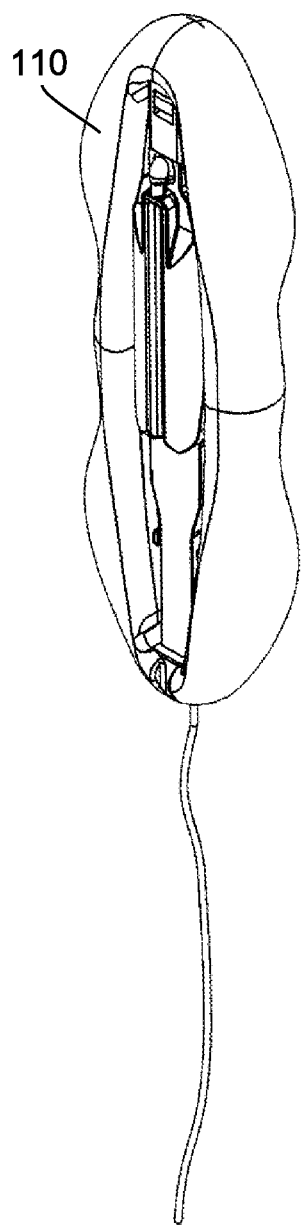
FIGS. 2A and 2B are perspective views of the device of FIG. 1 in a collapsed state and an expanded state, respectively, in accordance with an exemplary embodiment of the invention.
Figure 2B:
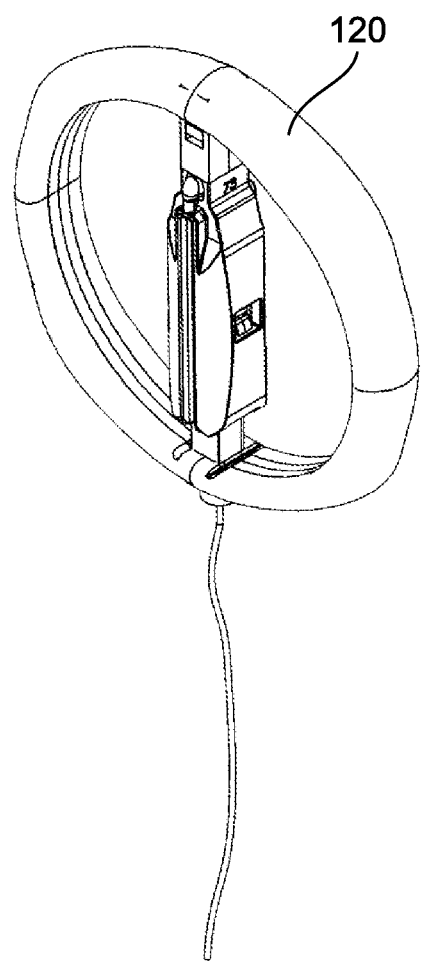

The present invention, in some embodiments thereof, relates to the health care industry and, more particularly, but not exclusively, to devices and methods for treating feminine pelvic organ prolapse.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways. It should also be understood that in this specification, "distal" or "distally" means in the direction of or on the side of the cervix and "proximal" or "proximally" means in the direction of or on the side of the vaginal introitus. In this application, the "second" end or side corresponds to the distal side and the "first" end or side corresponds to the proximal side of the device and/or applicator.

The Devices Generally

In general, devices and methods are described for the treatment of feminine pelvic organ prolapse. It should be understood that features, forms and/or functions overlap among some or many of the embodiments that will be described herein and that description in relation to one embodiment may also apply to others. For brevity and efficiency, many of these common features and/or forms and/or functions are described only in this "Generally" section but apply to one, some or all embodiments. Specific distinctions between embodiments in features, form and/or function are described in additional sections below.

In some embodiments of the invention, the devices described herein are generally planar (extend substantially in 2 dimensions) and exhibit an un-forced and/or naturally closed, compacted or collapsed state. In some embodiments of the invention, the device is substantially ring or circular shaped, although the device could also be rhomboid, ovoid, drop-shaped, multi-sided (hexagonal, pentagonal, octagonal, etc.), as examples. Different exemplary device embodiments are described in detail below, at least with respect to FIGS. 1-15D and FIGS. 37A-41.

The device, or at least the ring portion of the device, is constructed of a bio-compatible material or materials and, optionally, of a material or materials which do not facilitate vaginal flora changes. Exemplary materials include high density polyurethane (for the plastic/skeletal part) and thermoplastic elastomers or silicone for the cover. In some embodiments of the invention, the device is configured to be permeable or to allow vaginal secretions to exit the vagina.

In some embodiments of the invention, the external surface of the device is smooth, for example to increase comfort to the user, reduced accumulated discharge and/or reduce the production of biofilms.

In an embodiment of the invention, the ring is at least partially covered by a padding or exterior layer (which would then be the external surface of the device, taking the place of the ring itself as the external surface). Optionally, the layer is configured to at least enhance user comfort and/or to reduce or prevent tissue necrosis. Optionally, the layer is configured to permit vaginal secretions to exit the vagina. In an embodiment of the invention, the layer is elastic. Optionally, the layer is rigid.

In some embodiments of the invention, a removal string is operatively connected to the device to enable a user to displace the device from the vagina and remove it from her body.

In an embodiment of the invention, a locking mechanism is provided to the device, for example to enable the device to lock into an expanded and/or closed state. Different exemplary locking mechanism embodiments are described below, at least with respect to FIGS. 6A-B, 16-25B. In some embodiments of the invention, the device is bi-stable. Optionally the bi-stable feature is facilitated by the locking mechanism. In some embodiments of the invention, the locking mechanism is activated by an applicator used for inserting the device. Different exemplary applicator embodiments are described below, at least with respect to FIGS. 3A-B, 26-36. In some embodiments of the invention, the locking mechanism is deactivated by the removal string. In some embodiments of the invention, the locking mechanism is activated and/or deactivated by something other than mechanical forces, for example using magnetic, electric, pneumatic, and/or hydraulic force.

The devices described herein are configured to accommodate a plurality of vaginal sizes and/or shapes, in some embodiments of the invention. For example, the devices optionally are provided in a variety of sizes and/or shapes and/or flexibilities. In some embodiments of the invention, determination of which specific device is most appropriate for a certain user is performed by a sizing device configured for indicating a device size to the user or to an attending medical professional. In some embodiments of the invention, the sizing device changes diameter and/or configuration to known device sizes and/or configurations in order to determine the proper device that should be used by the user. In some embodiments of the invention, a "fit-kit", comprised of a plurality of different sized devices (or dummies representing different device sizes), is used by the physician, or by the patient to self-diagnose, to find the proper size by trying out the different sizes until the most appropriate one is found. In some embodiments of the invention, an attending medical professional uses the fit-kit. In some embodiments of the invention, the devices are provided in a set of specific sizes, for example 61-67-73-79-85-91 mm, where the sizes vary by a set amount (i.e. 6 mm) However, in some embodiments of the invention, the device sizes vary by different amounts, for example the sizes may vary by 3-10 mm between different sizes.

In some embodiments of the invention, device shape is predefined but not permanent, that is, once deployed inside the patient the flexibility of the device allows some shape matching to the user's individual anatomical features. In some embodiments of the invention, the device exhibits an expanded diameter of 55-97 mm, depending on the embodiment. In some embodiments of the invention, the devices exhibit collapsed or compacted diameters of 20-40 mm. In some embodiments of the invention, the device does not exhibit a uniform flexibility around the circumference of the ring. For example, the ring is rigid at 0° and 180° (points corresponding to the axis of the locking mechanism or the axis of insertion using an applicator) but is flexible at all other points. As another example, the ring is rigid at 0° and 180°, is less rigid at 90° and 270° and is flexible elsewhere. In some embodiments of the invention, the ring increases in rigidity towards 0° and 180° and increases in flexibility towards 90° and 270°. In some embodiments of the invention, the ring is configured such that mirror image portions of the ring (any subsection up to and between 180°) flex towards each other, for example at 45 and 135 degrees and/or at the exact opposite. In some embodiments of the invention, the ring exhibits alternating, regular rigidity and/or flexibility around the circumference of the ring. In some embodiments of the invention, flexibility of the ring corresponds to planes of flexibility.

It should be understood that these are examples only, and that any combination of rigidity and flexibility, including no rigidity or no flexibility are permitted, depending on the intended use and/or needs of the user.

In some embodiments of the invention, sizes and/or shapes and/or flexibilities are chosen to reduce pressure on vaginal walls and/or provide better force distribution of the device on vaginal walls and/or to reduce the probability of pressure necrosis, optionally in combination with the padded cover/exterior layer.

In some embodiments of the invention, the device and the applicator, together, comprise a system for inserting and deploying the prolapse alleviating device.

In some embodiments of the invention, the device and/or the applicator is disposed of after use. In some embodiments of the invention, the device is reusable and/or configured to be reused (for example, is washable/sterilizable). In some embodiments of the invention, at least a component of the applicator is reusable, for example a holder element and/or a pushing element.

Function and Modes of Operation

In some embodiments of the invention, operation of the devices described herein can be divided into three general phases: i.) insertion, ii.) use (i.e. wearing the device), and iii.) removal.

With respect to insertion, devices are inserted with a particular predetermined orientation (or with orientation assistance) or are not sensitive to insertion orientation, depending on the particular embodiment. In some embodiments of the invention, devices described herein are inserted in a closed, compacted and/or collapsed state for ease of storage and/or insertion.

In some embodiments of the invention, devices are inserted manually, without an applicator. Optionally, the user or a caregiver inserts the device manually. In some embodiments of the invention, devices are inserted with an applicator, which optionally also assists with orientation. In some embodiments of the invention, depth of insertion is a factor to be considered. Optionally, an applicator used for inserting a device is configured, for example the grip of the applicator is located such that proper insertion depth is established when the patient inserts the device until the fingers holding the applicator touch the labia. In some embodiments of the invention, the applicator is disposed of after device insertion and/or deployment.

In some embodiments of the invention, at least one of the devices (optionally including an applicator) described herein is configured to be inserted and/or deployed with only one hand. In other cases the applicator may be held with two hands (fingers 1+3 of both hands, and the plunger pushed forward with the 2 index fingers, or held with two hands and plunger pushed with one index finger. In some embodiments of the invention, at least one device (optionally including an applicator) is configured to be insertable and/or deployable regardless of the user's position, for example while the user is in a supine, standing or sitting position. In some embodiments of the invention, at least one device (optionally including an applicator) is configured to be insertable and/or deployable minimizing user self-touching. For example, the user does not have to separate the labia in order to insert the device and/or does not need to insert fingers into the vagina in order to position the device.

In some embodiments of the invention, the device is configured to properly position and/or orient itself into treatment rendering position during and/or after insertion. For example, the device is designed so that if the user inserts the device as instructed, with both parts of the applicator facing anteriorly and posteriorly, the device will always position itself bilaterally within the vagina. In addition, vaginal muscles will turn the device to the correct position, even if unintentionally it was inserted the wrong way.

With respect to usage of the devices described herein, in some embodiments of the invention they are inserted into the user in order to treat pelvic organ prolapse and/or to support the vaginal walls, that is, to provide support from the vagina against organs sagging down into the vaginal canal. In some embodiments of the invention, devices described herein are expanded and/or change state for use. In some embodiments of the invention, the devices described herein treat pelvic organ prolapse by stretching vaginal walls, optionally laterally, flattening the anterior and posterior vaginal walls and thereby reducing anterior and posterior prolapse. In some embodiments of the invention, any structure in the center of the ring of a device also passively assists the treatment of prolapse by inhibiting further decent into and through the center of the ring, for example an internal locking mechanism 138, shown in FIG. 7B. In some embodiments of the invention, a space occupying characteristic of the devices described herein treat apical prolapse, whereby the vaginal apex (uterine/vault) is not allowed to descend. The devices described herein are removed after insertion periodically. Optionally, the devices herein are reusable. In some embodiments of the invention, the devices described herein are configured to elute pharmaceutical substances into the user.

With respect to removal of the devices described herein, the devices change from an expanded and/or deployed state into a closed, compacted and/or collapsed state for ease of removal. Optionally the removal state/configuration is the same as the storage/insertion state/configuration. In some embodiments of the invention, removal is effectuated by pulling on a removal string which is operatively connected to the device. Optionally, forces applied to the removal string are configured to also cause state/configuration change of the device from an expanded state to a collapsed state. Optionally, in cases where vaginal walls are lax, a pull of the string will cause extraction of the device still in its deployed state, somewhat deformed due to its flexibility, before the pulling force on the locking mechanism comes into action. This depends on the resistance of the vaginal introitus, and when absent—the device may be removed painlessly and/or without collapse.

Exemplary Device Embodiments

Referring now to the drawings, FIG. 1 is a perspective view of prolapse treating device 100 with a diamond shaped snapping element (shown in FIGS. 7A-7C) attached to an applicator 200, in accordance with an exemplary embodiment of the invention. The device 100 is configured to transform between two configurations or states, a flexible, reduced profile insertion/storage/removal configuration 110, shown in FIG. 2A, and substantially rigid (or at least more rigid than the reduced profile configuration) ring-like expanded configuration/state 120, shown in FIG. 2B, designed to provide support of prolapsed organ from within the vagina.

The applicator 200 is attached to the device 100 and used for insertion the device 100 into a vagina and/or for transforming the device 100 from the collapsed insertion configuration 110 into the expanded, ring-like configuration 120, in some embodiments of the invention. In the position shown in FIG. 1, a pusher 240 (described in more detail with respect to FIG. 3A) is positioned backward and the device 100 is held by a holder 220 (described in more detail with respect to FIG. 3A) in its collapsed state 110.

Figure 3A:
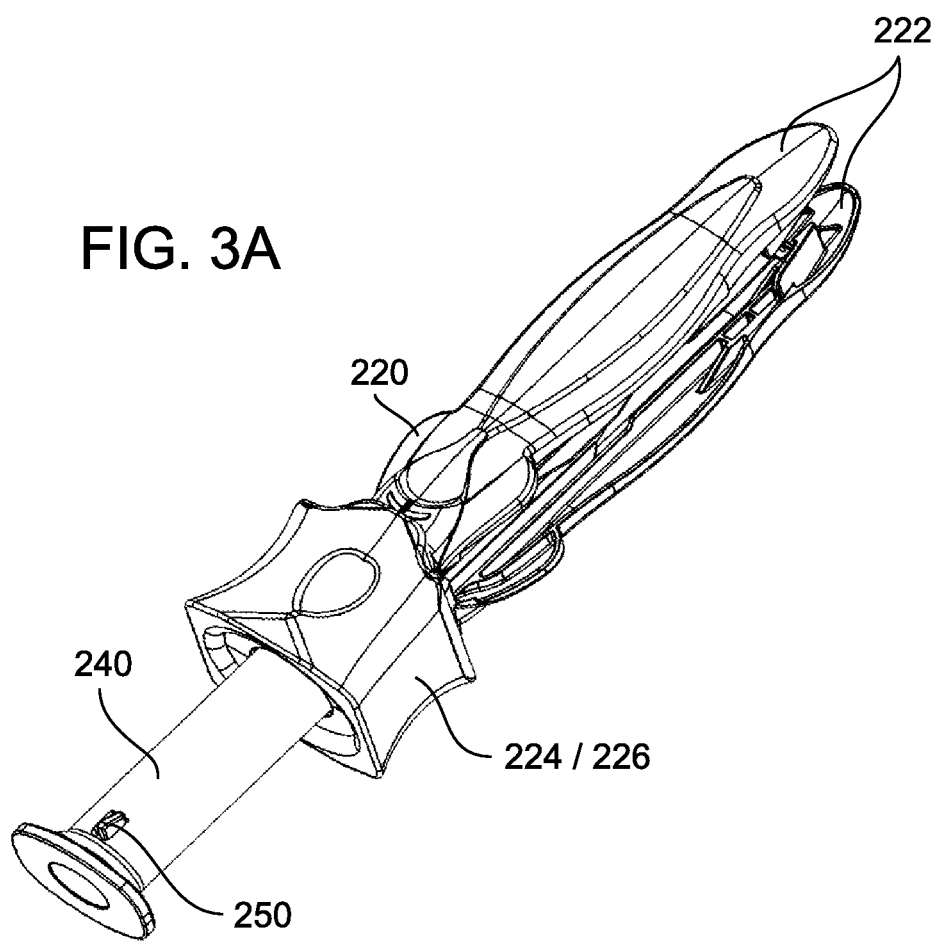
FIGS. 3A and 3B are perspective views which show in more detail the pushing and holding elements of the applicator of FIG. 1, in accordance with an exemplary embodiment of the invention.
Figure 3B:
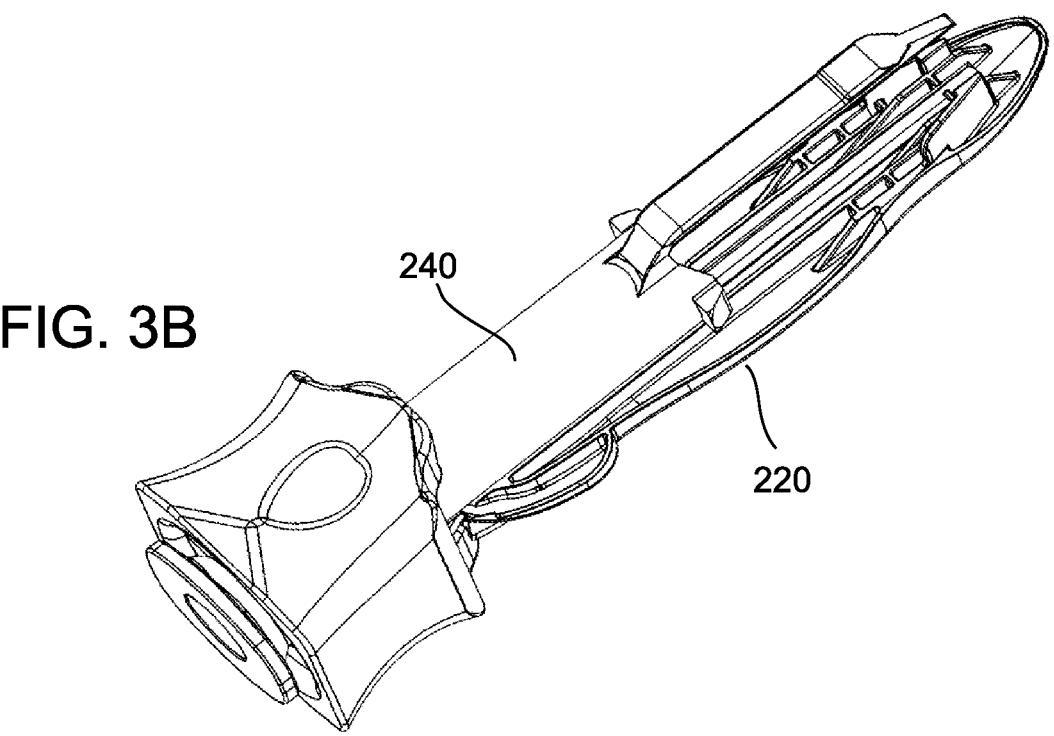
Figure 4:
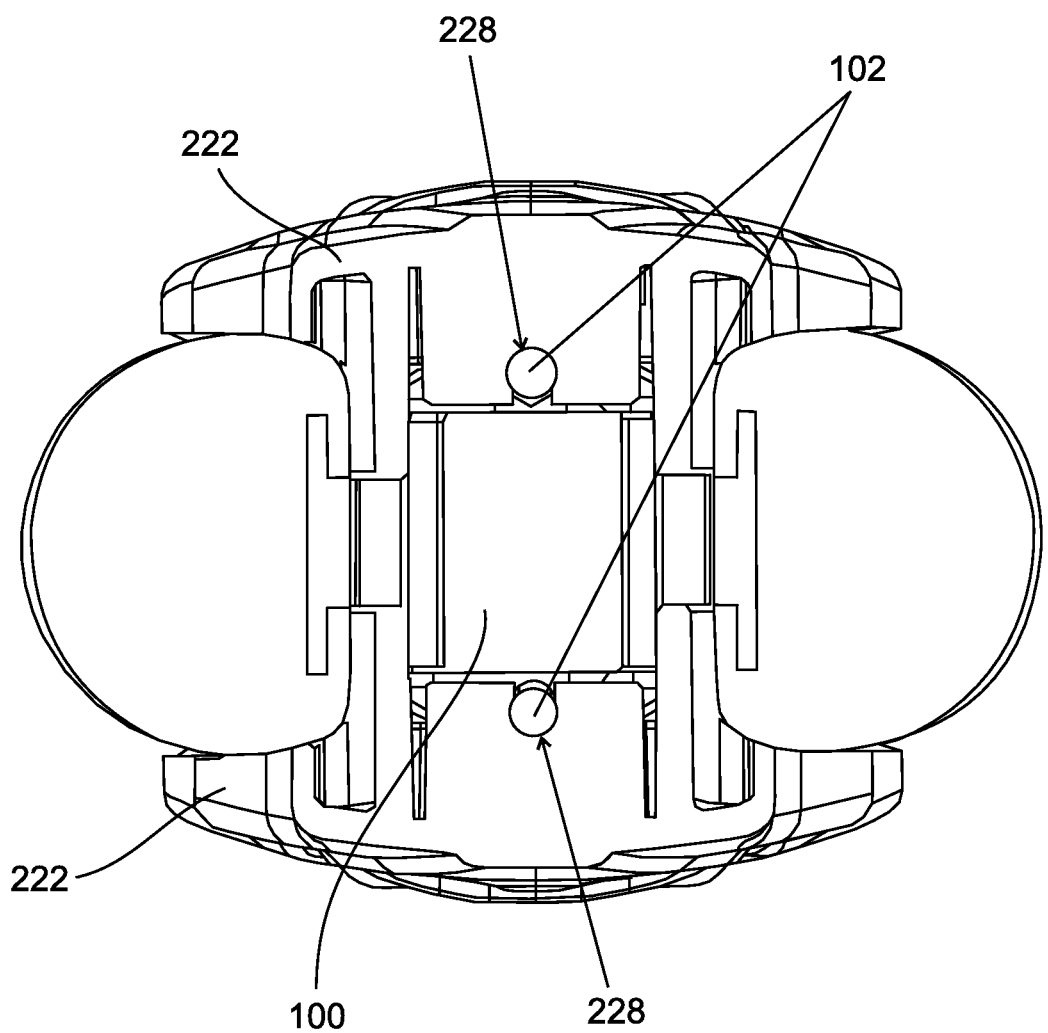
FIG. 4 is a cross-sectional top view of the device of FIG. 1, in accordance with an exemplary embodiment of the invention.
Figure 5:
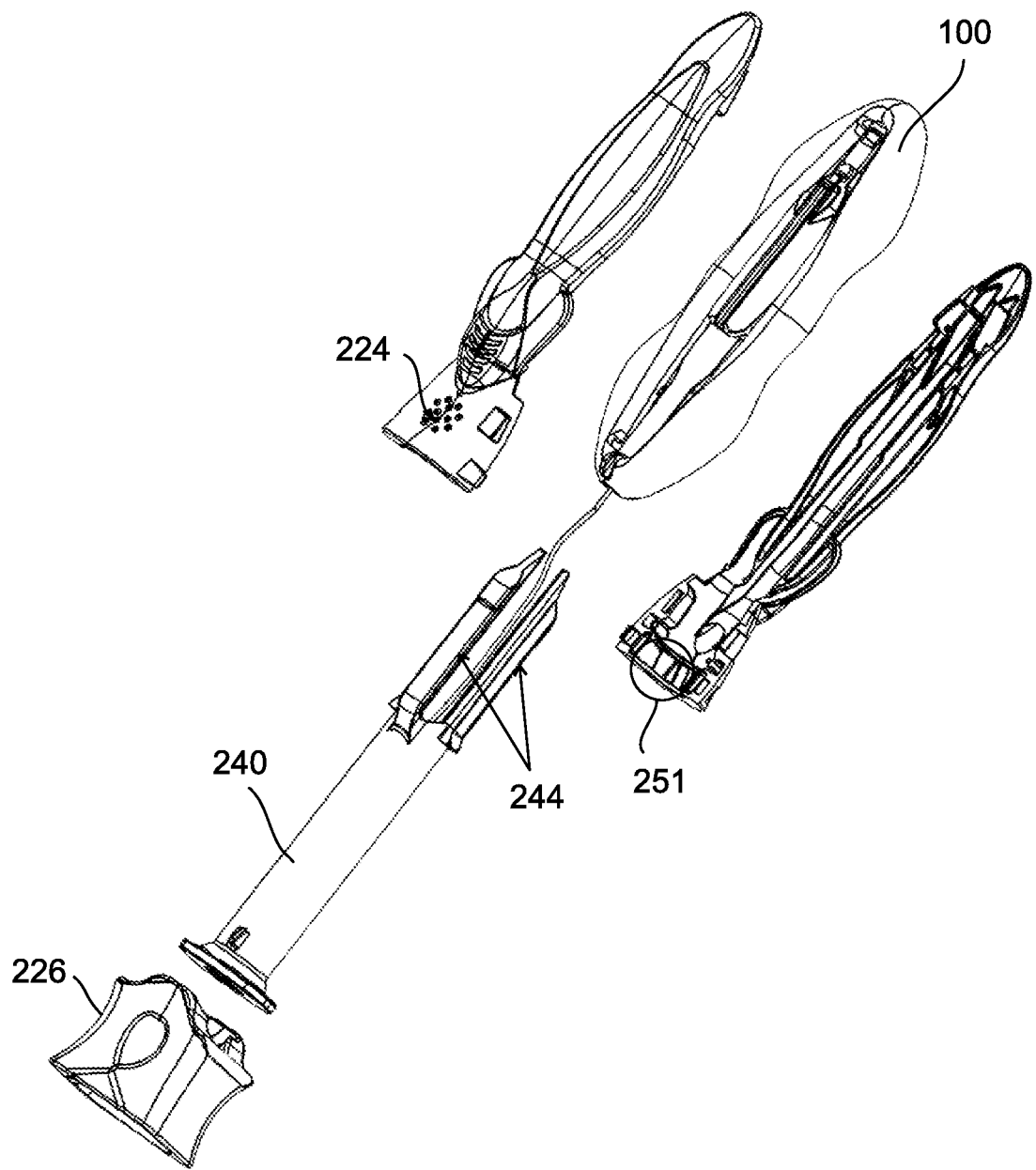
FIG. 5 is a partially exploded view of the device and applicator of FIG. 1, in accordance with an exemplary embodiment of the invention.

FIGS. 3A-3B are perspective views which show in more detail pusher 240 and holding elements 220 of the applicator 200 of FIG. 1, in accordance with an exemplary embodiment of the invention. The holder 220 and pusher 240 are assembled such that axial (the major axis) movement of the pusher 240 relative to the holder 220 is permitted. The pusher movement is led by guiding canals on the device (shown in FIGS. 2A-2B) The holder 220 may be built of two opposite wings 222, in an embodiment of the invention. Each of the holder wings 222 has a central groove 228 opened to the direction of the device by a neck (shown in FIG. 4). The device has mounds 102 on both sides fitting the holes of the holders. The device mounds 102 are held within the holder's grooves 228. In use, the user can hold the gripping area 224 with fingers 1 (thumb)+3 (middle), and push the plunger with finger 2 (index). For the convenience of the user the gripping area may be covered by a soft part—grip 226 (shown in FIG. 5). The pusher 240, shown in FIG. 5, has two protruding arms 244 with a sloped edge, in an embodiment of the invention. FIG. 5 is a partially exploded view of the device and applicator of FIG. 1, in accordance with an exemplary embodiment of the invention. In some embodiments of the invention, the gripping area 224 is configured with a length such that when the user inserts the applicator into her vagina, the location of the gripping area where the user's fingers are placed ensures that the device's ring center passes the Labia.

As described elsewhere herein, the device and/or the applicator are configured to be disposable, for example with a locking mechanism. In some embodiments of the invention, the hand-actuated end of the pusher 240, the proximal end, is provided with a biased locking nub 250 (angled to slide into a locking position and to prevent unlocking) which is designed as a counterpart to a fenestration 251 (shown in FIG. 5) which is located within the body of the wings 222 such that when the pusher 240 is advanced fully into the holder 220, the nub 250 locks into the fenestration 251 and prevents the retraction of the pusher 240 from the holder 220. In an embodiment of the invention, this configuration renders the applicator as a single use, disposable component. Optionally, the nub 250 and/or the fenestration 251 are not provided to the applicator elements such that the pusher 240 is retractable from the holder 220 after use, making the applicator reusable.

Figures 6A, 6B:
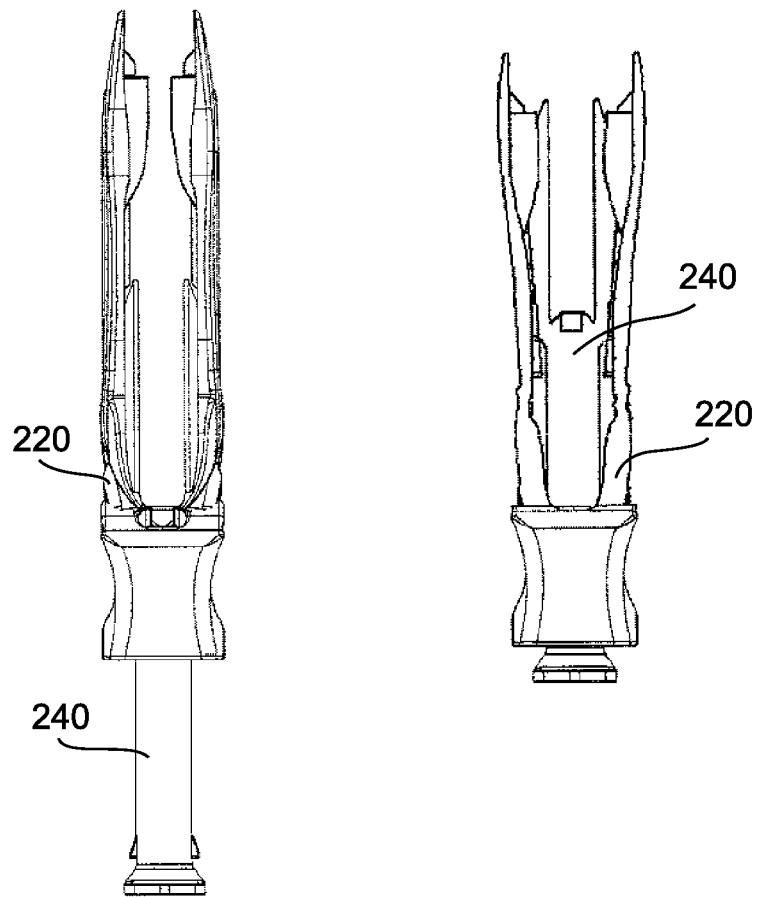
FIGS. 6A-6B are side views of the pushing and holding elements prior to deployment and after deployment and separation of the device from the applicator, respectively, in accordance with an exemplary embodiment of the invention.

FIGS. 6A-6B are side views of the pusher 240 and holder 220 prior to deployment and after deployment and separation of the device from the applicator, respectively, of the device 100 from the applicator 200, in accordance with an exemplary embodiment of the invention. In an embodiment of the invention, when the pusher 240 is moved within the holder 220 it presses the device 100 and gradually transfers the device 100 from its collapsed, stick-like configuration 110 to the ring like configuration 120—expanded position. When reaching the ring like configuration 120, the device 100 is locked by an internal locking mechanism 138 (shown in FIGS. 7A-7C). When the device 100 is locked, the sloped edges of the pusher 240 arms come in contact with the holder 220 wings and force them to bend outward (shown in FIG. 6B), disconnect the device mounds from the holder grooves and release the device 100.

Figure 7A:
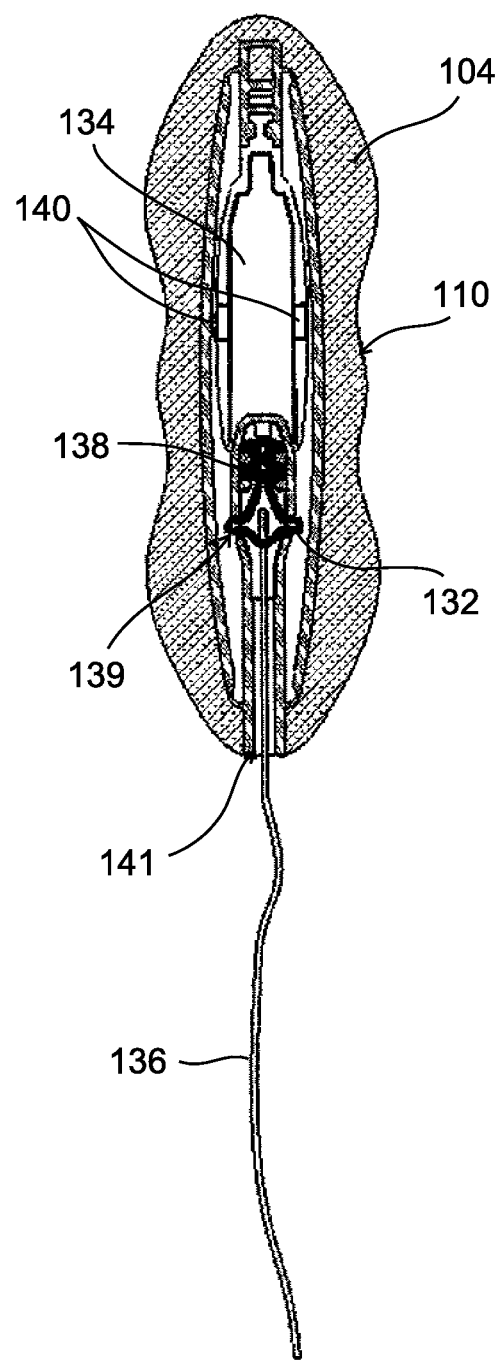
FIGS. 7A-7C are cross-sectional views of the device of FIG. 1 showing operation of a locking mechanism with snapping elements, in accordance with an exemplary embodiment of the invention.
Figures 7B, 7C:
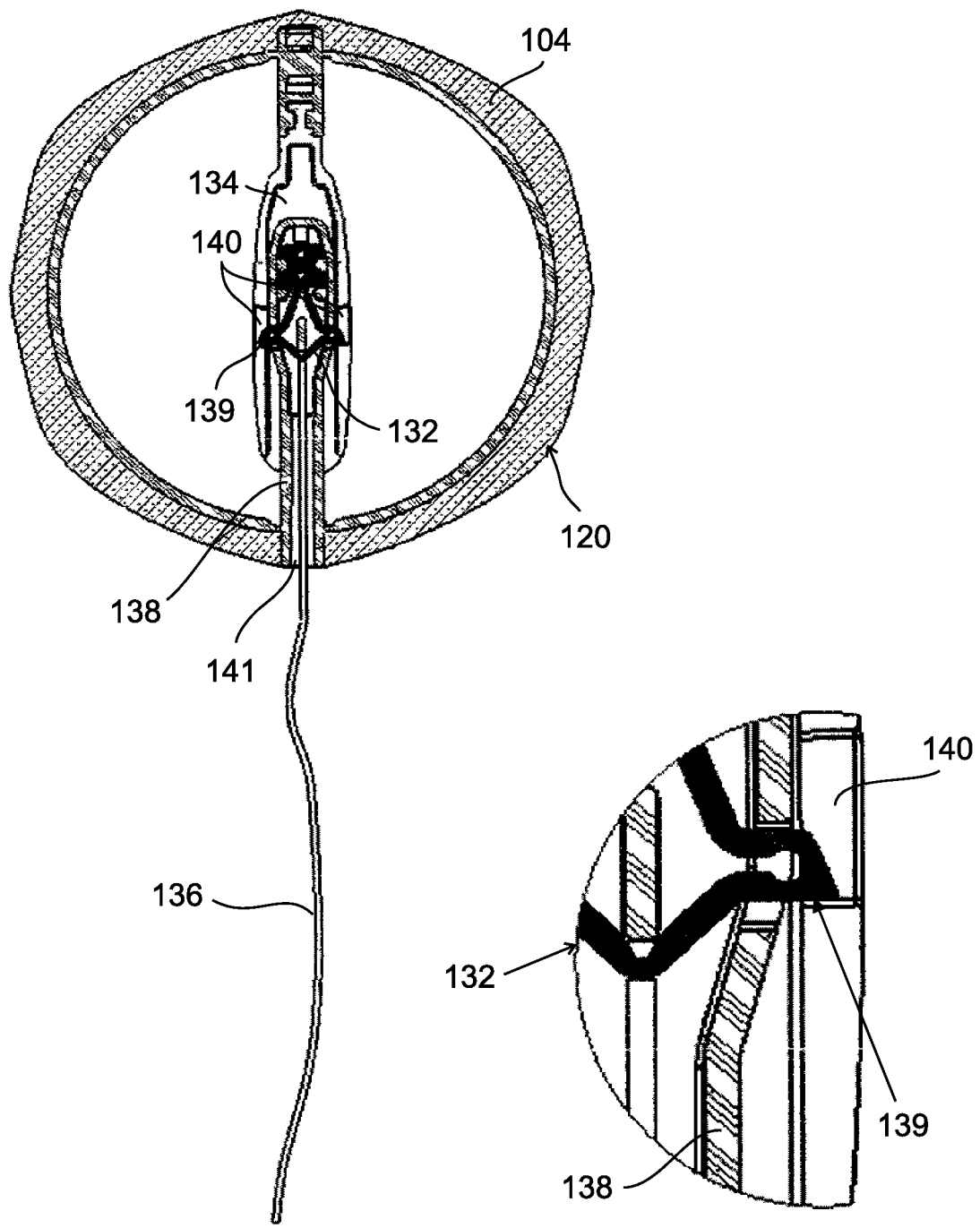

FIGS. 7A-7C are cross-sectional views of the device of FIG. 1 showing operation of the locking mechanism with snapping elements, in accordance with an exemplary embodiment of the invention. The locking mechanism is made of a telescopic system having a first element 138 comprising a flexible and elastic diamond shape 132. Optionally, the first element is tube shaped except for the elastic diamond snapping element portion.

The second element 134 (also optionally tube shaped) contains windows 140, and the first element is configured to slide axially within the second element (e.g. a tube within a tube). The elastic diamond is compressed so that it slides inside the second element until at least one prong 139 of the diamond snapping element 132 reaches at least one window 140. Optionally, there are two prongs 139 and counterpart windows on opposing sides of the central axis. Optionally, there are a plurality of prongs and counterpart windows. The prongs 139 of the diamond snapping element 132 are released into the windows (due to the elastic nature of the diamond element 132), thus locking the device into the expanded state 120 and returning the diamond shape 132 to its normal uncompressed form.

In an embodiment of the invention, the applicator 200 is then pulled backwards, outside of the vagina while the device 100 is left inside in its expanded state.

A removal string 136, is operatively connected to the diamond 132, in an embodiment of the invention. When the applicator 200 is removed, the proximal end of the removal string is left outside the vagina (like the string of a menstrual tampon) by passing from the diamond 132 in a proximal direction through a central channel 141 in the device 120 and central channel in the pusher 240. By pulling the removal string 136, the diamond 132 is compressed towards a central axis of the locking mechanism thereby also pulling the prongs 139 towards the central axis and out of the windows 140. In an embodiment of the invention, this releases the locking mechanism causing a state change to a compressed state 110 and allows easy removal of the device 100 from the vagina.

FIGS. 7A and 7B show the padding or exterior layer 104 covering the more rigid ring 102 of the device 100.

Figure 8A:
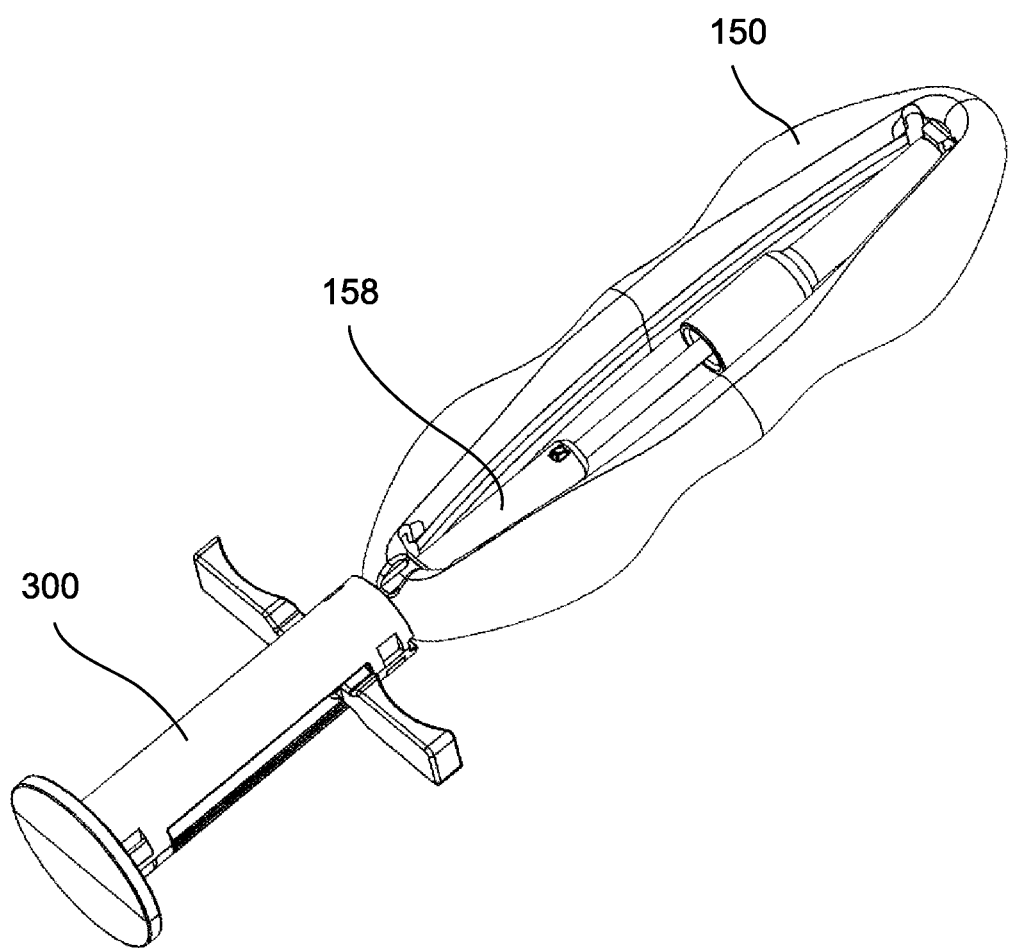
FIG. 8A is a perspective view of a prolapse treating device with a double side snapping tube with an internal applicator, in accordance with an exemplary embodiment of the invention.

FIG. 8A is a perspective view of a prolapse treating device 150 with a side snapping internal tube 158 (shown in more detail in FIGS. 10A-10B) and with an internal applicator 300, in accordance with an exemplary embodiment of the invention. As with many other embodiments described herein, the device 150 is configured to assume a plurality of stable states (e.g. compressed and expanded).

Figure 8B:
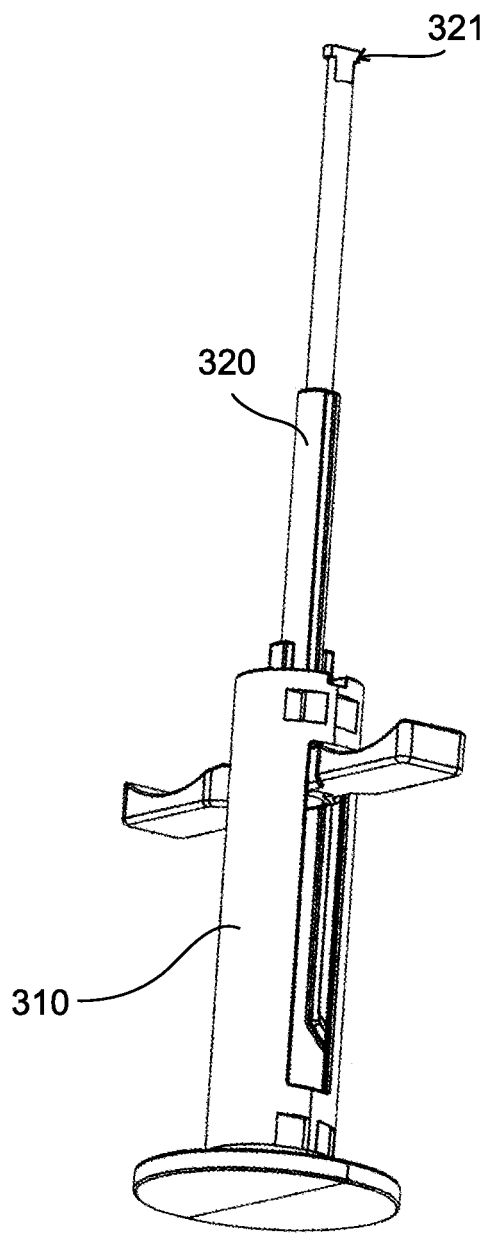
FIG. 8B is a perspective view of the internal applicator of FIG. 8A, in accordance with an exemplary embodiment of the invention.

FIG. 8B is a perspective view of the internal applicator 300 of FIG. 8A, in accordance with an exemplary embodiment of the invention. In an embodiment of the invention, the applicator 300 comprises at least two components: a holder 310 and a puller 320. The holder 310 and puller 320 are assembled in a way that allows axial movement of the puller 320 relative to the holder 310. In an embodiment of the invention, the puller 320 has two locking teeth 321 that protrude outward (from a central axis of the device/applicator) at its distal end. When pulling the puller 320, it pulls the device's distal side towards the proximal side and gradually transfers the device from its first, collapsed configuration (FIG. 10A) to the expanded ring-like configuration (FIG. 10B). The puller's locking teeth 321 are released after the transition to the device's ring configuration is completed, in some embodiments of the invention—see detailed description below.

Figure 8C:
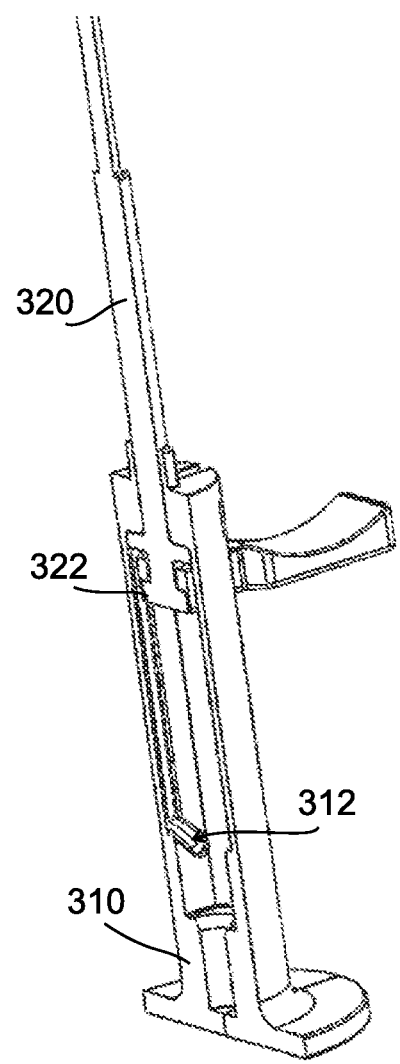
FIG. 8C is a cross-sectional view of a holder element of the applicator of FIG. 8A, in accordance with an exemplary embodiment of the invention.

FIG. 8C is a cross-sectional view of a holder 310 element of the applicator of FIG. 8A, in accordance with an exemplary embodiment of the invention. The holder 310 has an internal leading rail 312 with a rotation at its proximal end. In an embodiment of the invention, the puller 320 has two protruding teeth 322 on its proximal end that slide within the holder's internal leading rail 312. When these teeth reach the end on the leading rail the puller 320 is rotated and allows detachment of the locking teeth 321 from the device, in an embodiment of the invention.

Figure 9:
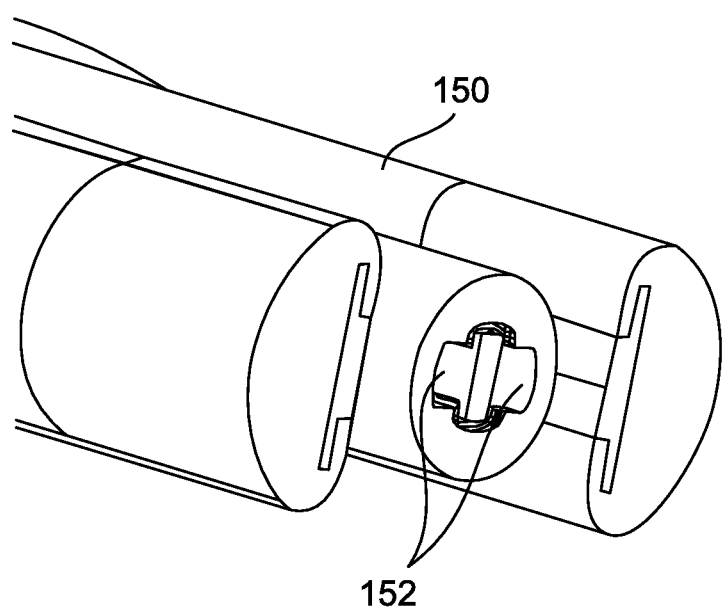
FIG. 9 is a short axis cross-sectional view of the device of FIG. 8A, in accordance with an exemplary embodiment of the invention.

FIG. 9 is a short axis cross-sectional view of the device 150 of FIG. 8A, in accordance with an exemplary embodiment of the invention. In some embodiments of the invention, the device 150 has internal locking area with two openings 152 that holds the puller's 320 locking teeth 321 as long as the puller 320 is not rotated, when the puller 320 is rotated the locking teeth 321 are released through the openings 152.

Figure 10A:
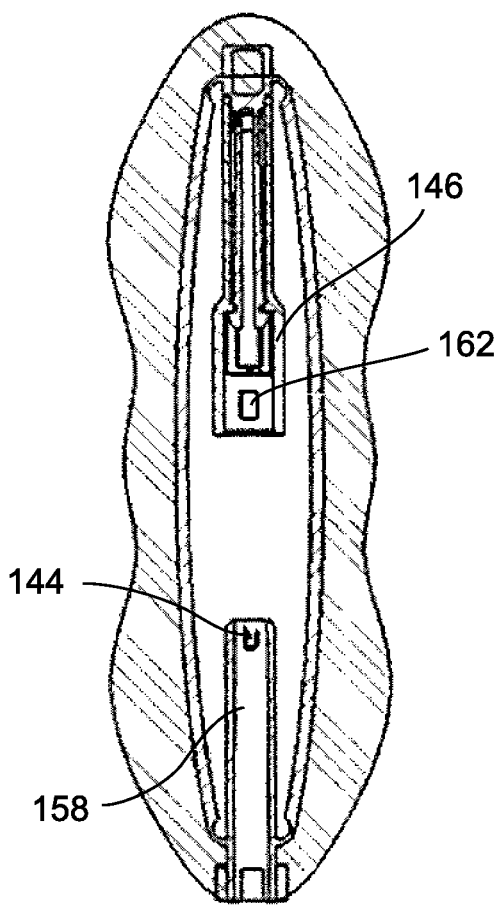
FIGS. 10A-10B are cross-sectional views of the device of FIG. 8A, showing operation of a locking mechanism with a double side snapping tube, in accordance with an exemplary embodiment of the invention.
Figure 10B:
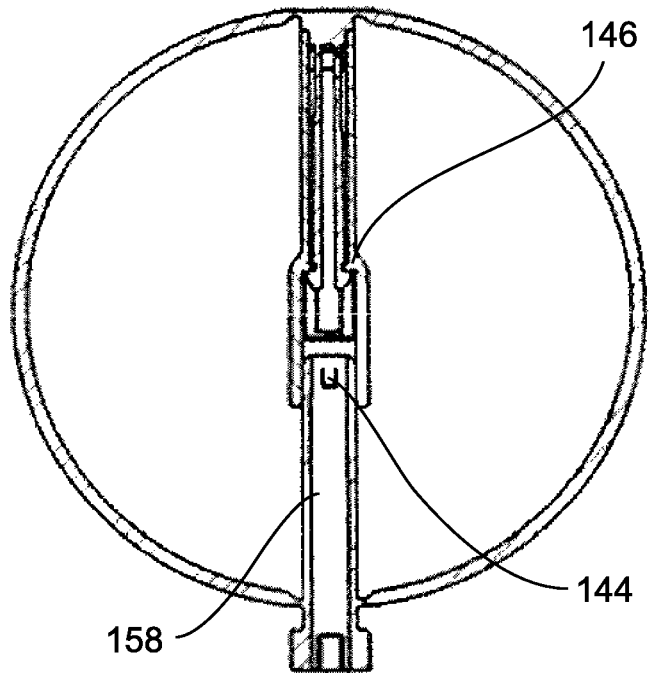

FIGS. 10A-10B are cross-sectional views of the device 150 of FIG. 8A showing operation of a locking mechanism with a tube configured with snapping elements 144, in accordance with an exemplary embodiment of the invention. In an embodiment of the invention, the locking mechanism is made of a telescoping system that has snapping elements 144 on the side snapping inner tube 158 that snap into internal grooves 162 on an outer tube 146, thus locking the device 150 into the expanded state. After the device 150 is locked into the expanded state (shown in FIG. 10B), the applicator 300 is then pulled backwards, outside of the vagina leaving the device 150 deployed inside.

Figure 11A:
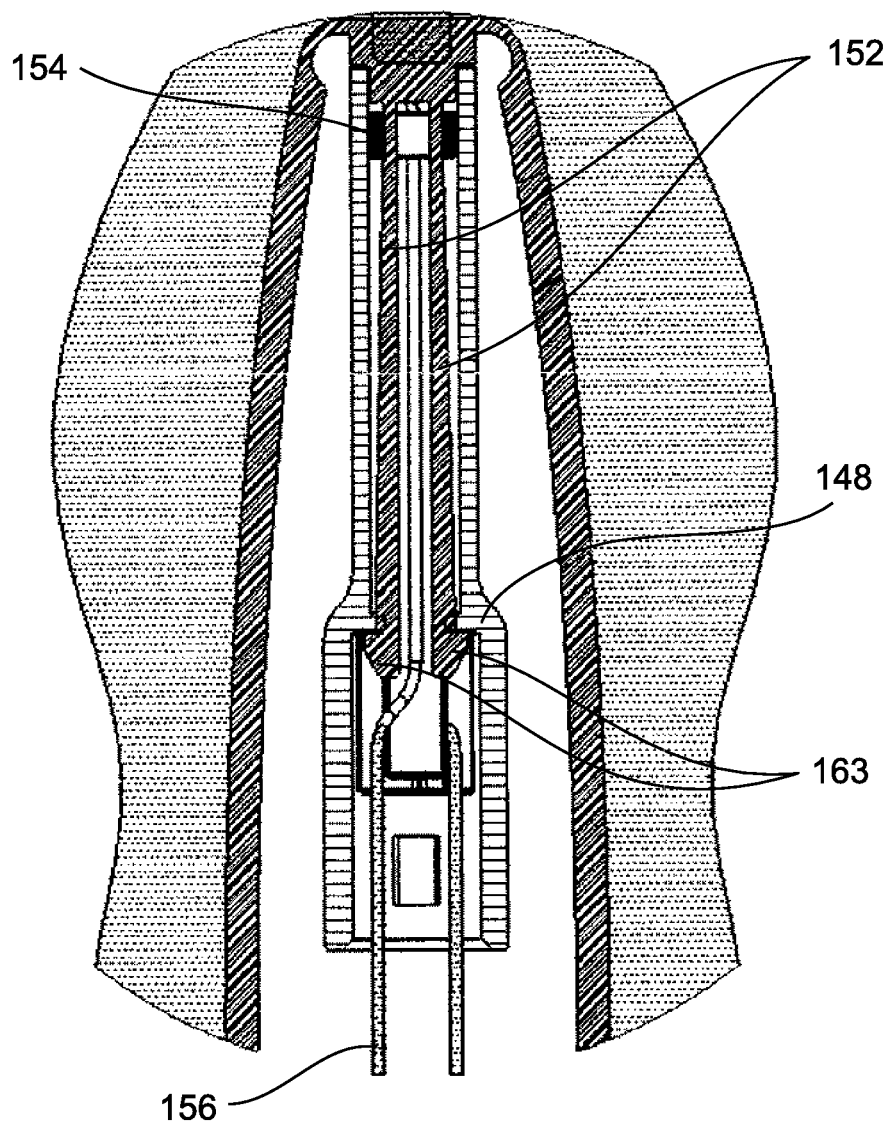
FIGS. 11A-11B are close-up section views of the removal mechanism of the devices of FIG. 8A or FIG. 10A in the usage and removal configurations, in accordance with an exemplary embodiment of the invention.
Figure 11B:
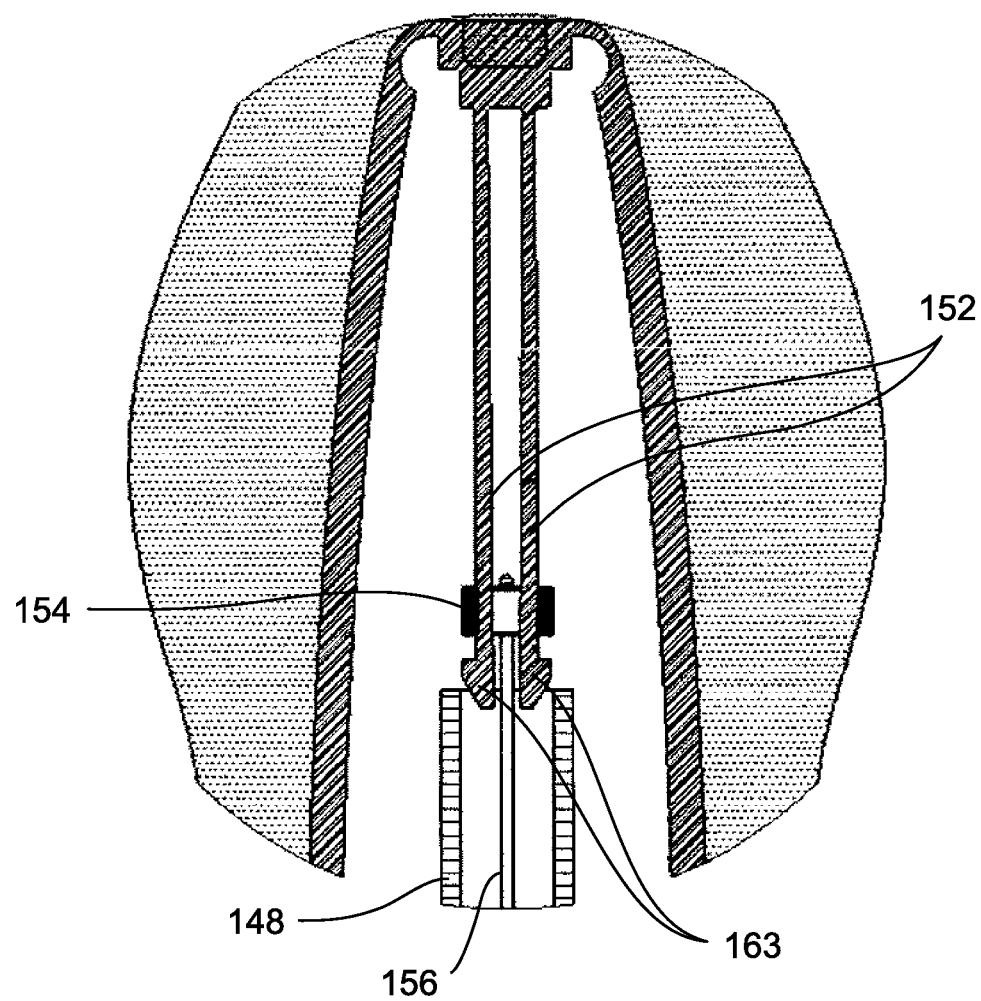

FIGS. 11A-11B are close-up views of the removal mechanism of the device of FIG. 8A in the usage and removal configurations, in accordance with an exemplary embodiment of the invention. In an embodiment of the invention, an outer telescopic tube 148 is connected to the ring 150 by two flexible arms 152 extending from the distal side of the ring towards the proximal side along the central axis of the device. Release snaps 163 are located at the proximal ends of the flexible arms 152, where the release snaps 163 releasably hold the outer tube 148. A release ring 154 is placed over the flexible arms 152. A removal string 156 is connected to the release ring 154 and passes through a central canal in the puller 320 and holder 310. As with other embodiments described herein, when the applicator 300 is removed the removal string's free end extends outside the vagina (similar to a conventional menstrual tampon). By pulling the removal string 156, the release ring 154 is pulled, bending the flexible arms 152 inwards. Bending the flexible arms 152 inwards releases the snaps 163 and detaches the outer tube 148 from the flexible arms 152, thus allowing the outer tube 148 to slide in a proximal direction (towards the vaginal introitus and away from the cervix) returning the device 150 to something akin to the collapsed state and facilitating easy removal of the device 150 out of the vagina.

FIGS. 12A-12C are front views of a device 400 with an internal pneumatic unit 402 with a pressure valve 420 (shown in FIGS. 13A-13C) connected by a detachable tube 404 to an air pump 406, in accordance with an exemplary embodiment of the invention. In an embodiment of the invention, pumping air through the inlet tube 404 into the pneumatic unit and gradually transforms the device 400 from a compressed configuration (shown in FIG. 12A) to the ring-like configuration (shown in FIG. 12B). In an embodiment of the invention, the pump 406 is disconnected from the device 400 after deployment.

Figure 13A:
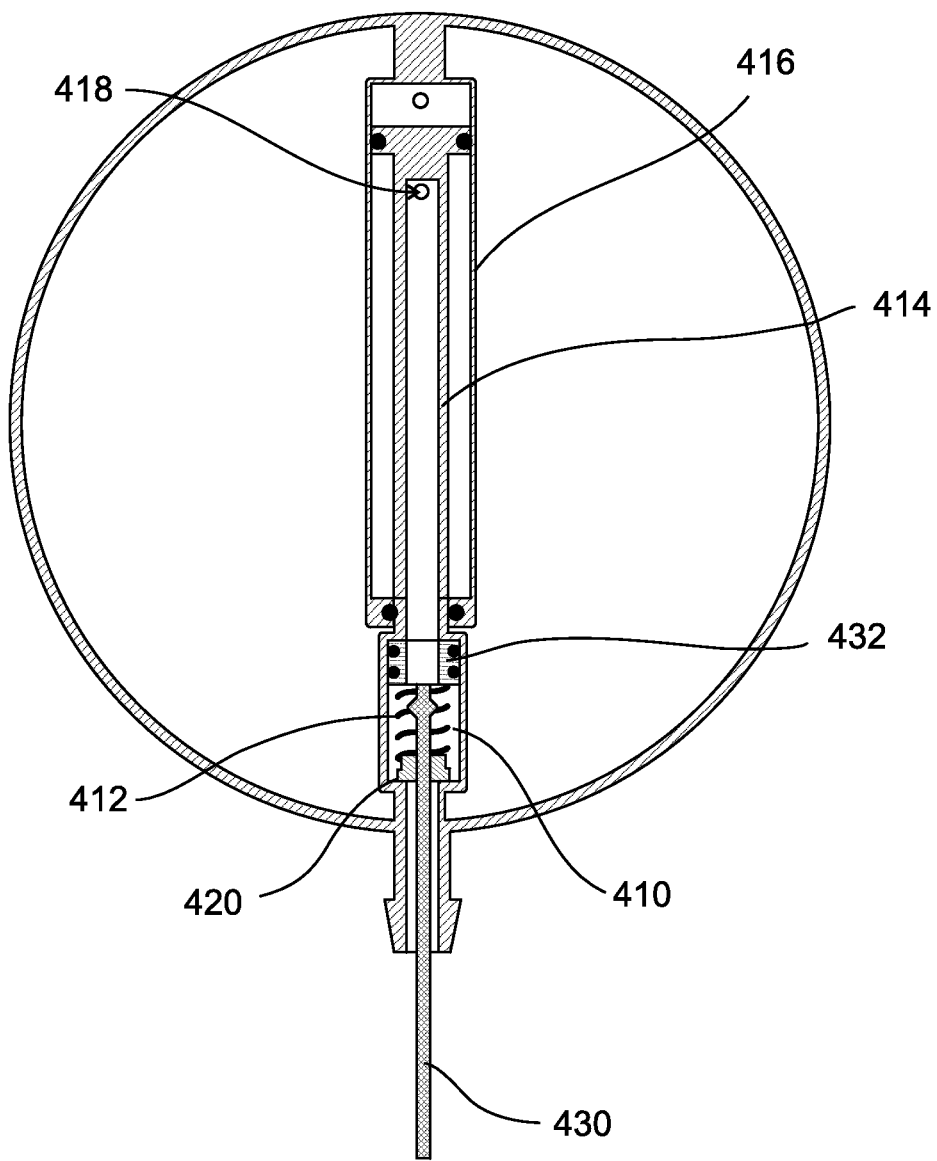
FIGS. 13A-13C are cross-sectional views showing the operation of the internal piston of the device shown in FIGS. 12A-12C, in accordance with an exemplary embodiment of the invention.
Figures 13B, 13C:
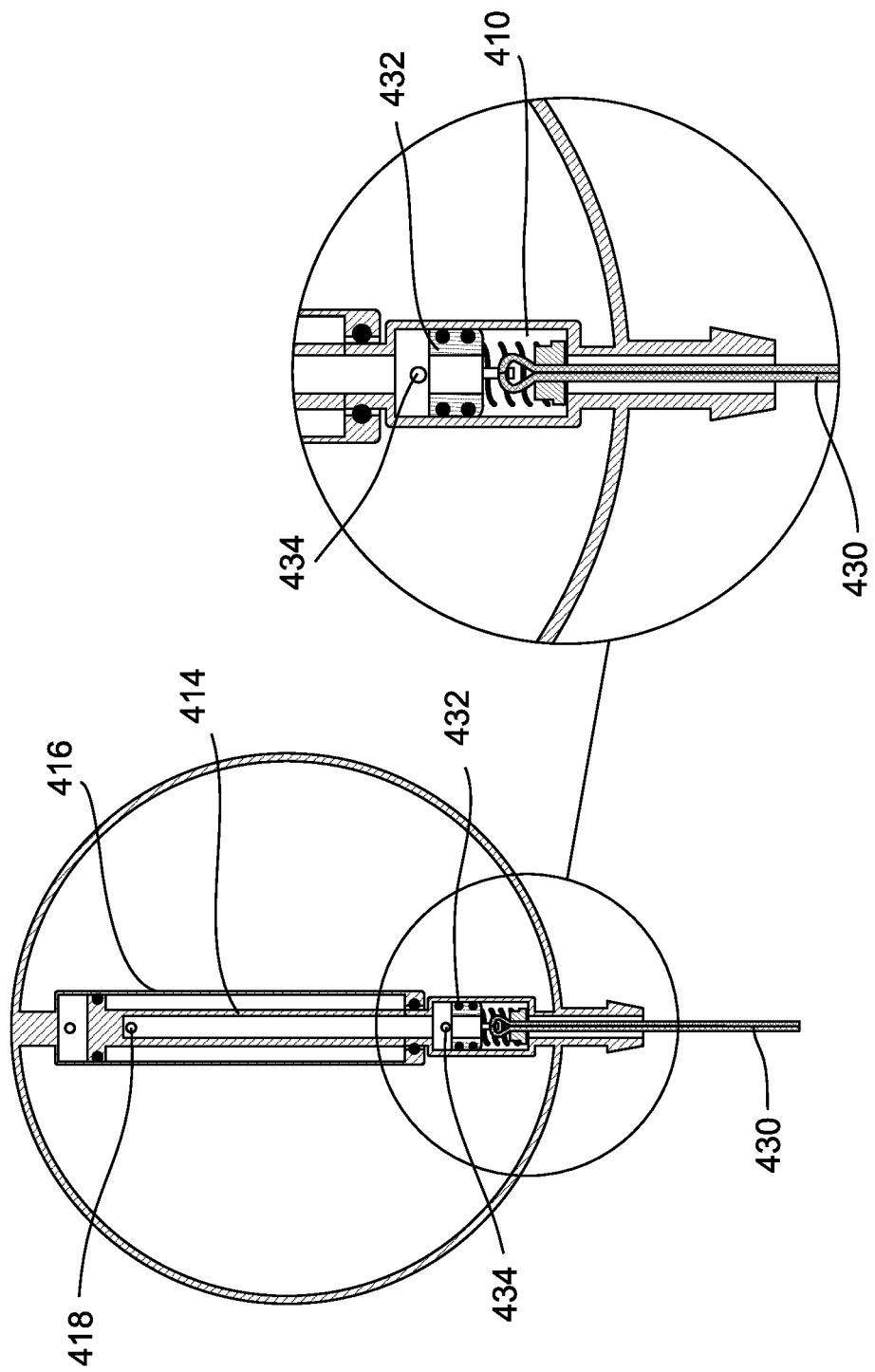

FIGS. 13A-13C are cross-sectional views showing the details of the internal pneumatic unit 402 of the device 400 shown in FIGS. 12A-12C, in accordance with an exemplary embodiment of the invention. Air passes from the air pump 406 through the detachable tube 404 and into a filling chamber 410. At the lower end of the filling chamber there is a valve 420 kept closed by a spring 412 thus preventing air from flowing back into the detachable tube. When the pump is pressed, air is pressurized and lifts the valve by compressing the spring thus enters the filling chamber and further flows into the pneumatic unit. The pneumatic unit comprises of a piston 414 connected to the device's lower side and a cylinder 416 connected to the device's upper side. From the pneumatic piston air enters the piston/cylinder space through holes 418 in the upper end of the piston.

In an embodiment of the invention, filling of the piston/cylinder space with air pushes the pneumatic piston towards the device's upper side thus transforming the device into a ring like configuration. The pressurized air within the cylinder holds the device in the ring like configuration.

In some embodiments of the invention, a removal string 430 is connected to the pressure release valve 432. By pulling the removal string 430 the valve 432 moves downwards and exposes drainage holes 434 in the filling chamber, thus releasing the pressurized air in the cylinder, releasing the piston and allowing the device to assume a state the same as or similar to the compressed state of FIG. 12A for easy removal of the device 400 out of the vagina.

In some embodiments of the invention, the detachable tube 404 also functions as the removal string 430.

In an embodiment of the invention, the pump 406 is disconnected from the device after deployment.

Figure 14A:
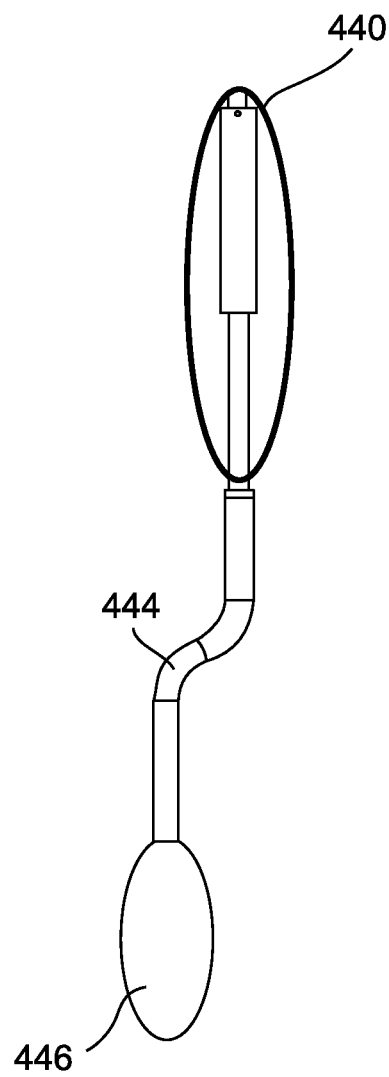
FIGS. 14A-14C are front views of a device with an internal piston with a snapping element connected by a detachable tube to an inflator, in accordance with an exemplary embodiment of the invention.
Figure 14B:
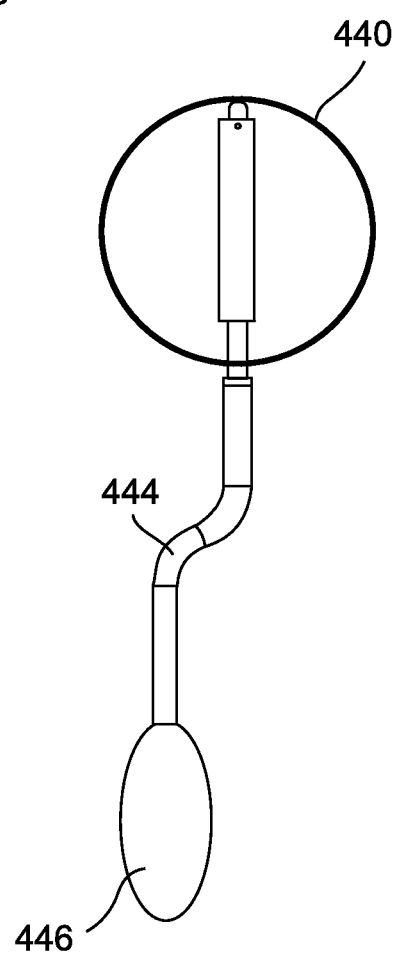
Figure 14C:
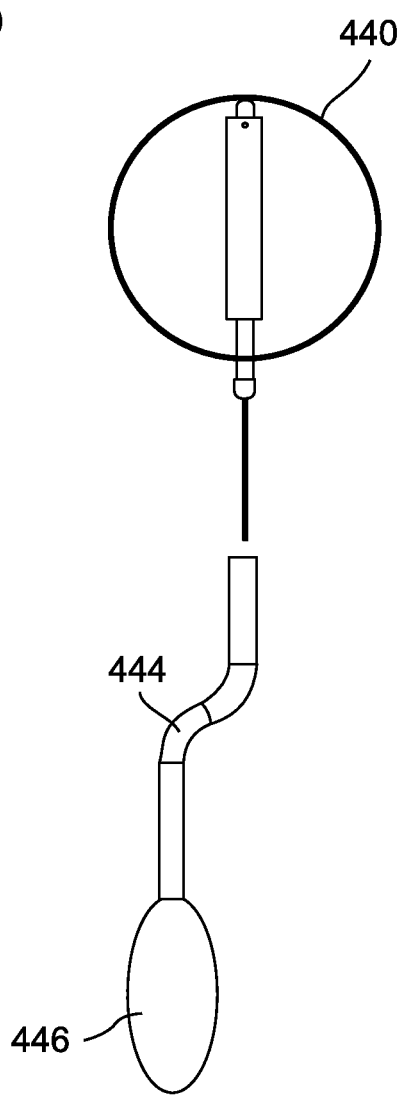

FIGS. 14A-14C are front views of a device 440 with an internal pneumatic unit 442 with a snapping element 448 (shown in FIGS. 15A-15D) connected by a detachable tube 444 to an air pump 446, in accordance with an exemplary embodiment of the invention. In an embodiment of the invention, pumping air through the detachable tube into the pneumatic unit and gradually transforms the device from a compressed configuration (shown in FIG. 14A) to the ring-like configuration (shown in FIG. 14B).

Figures 15A, 15B:
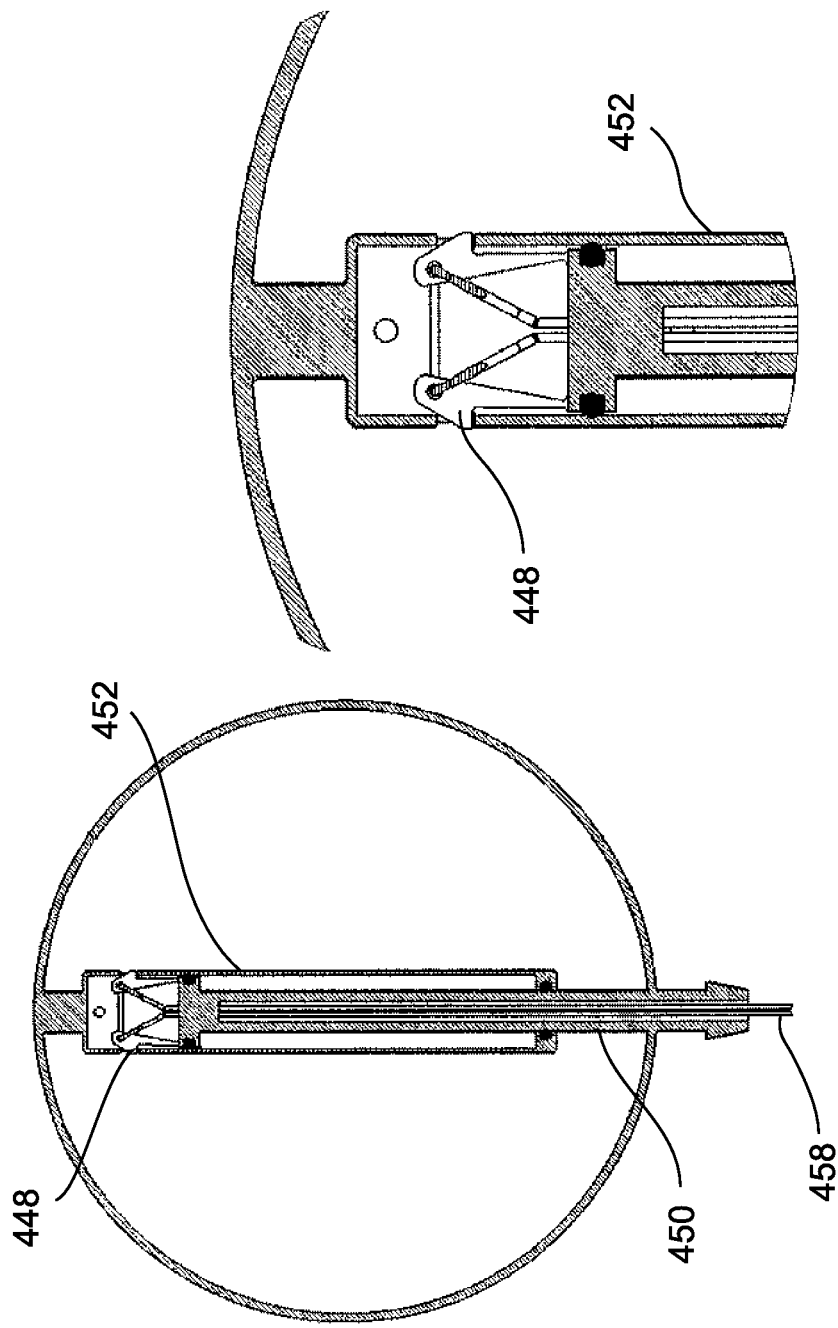
FIGS. 15A-15D are cross-sectional views showing the operation of the internal piston of the device shown in FIGS. 14A-14C, in accordance with an exemplary embodiment of the invention.
Figures 15C, 15D:
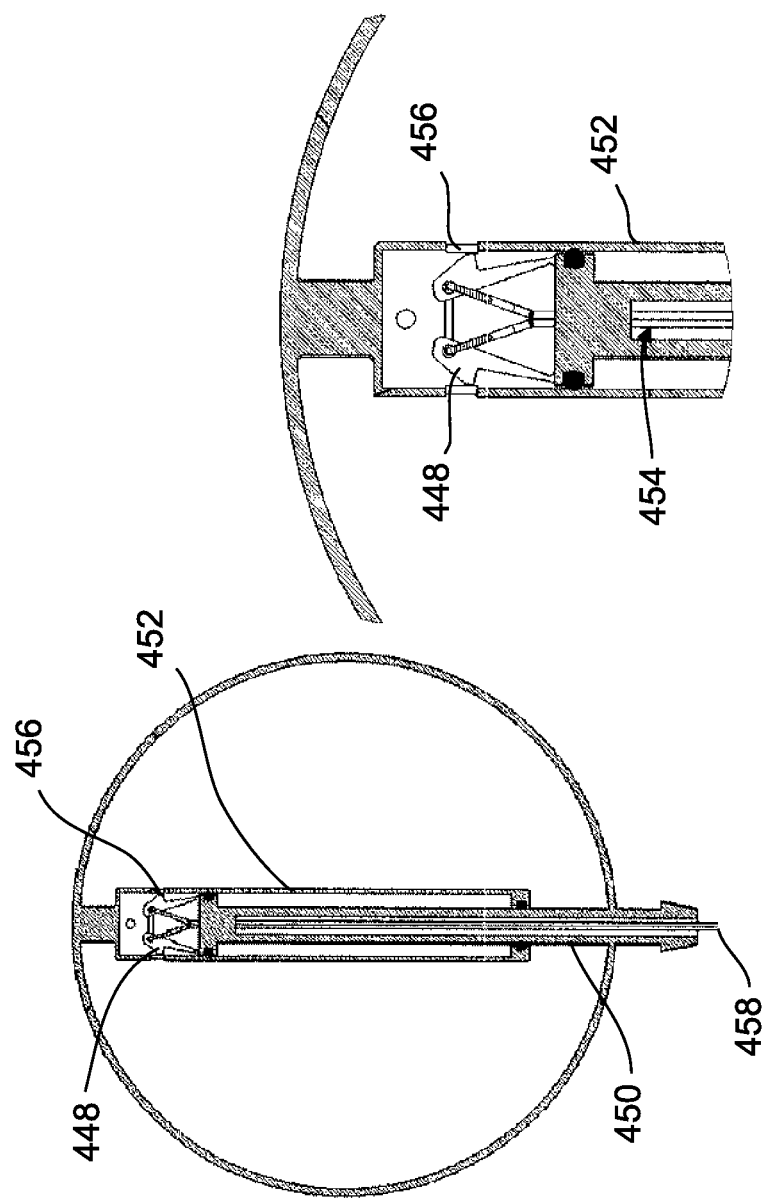

FIGS. 15A-15B are cross-sectional views showing the detail of the internal pneumatic unit 442 of the device 440 shown in FIGS. 14A-14C, in accordance with an exemplary embodiment of the invention. Air passes from the air pump 446 through the detachable tube 444 and into an internal piston 450. The piston is connected to the device's lower side while a cylinder 452 is connected to the device's upper side. The compressed air enters the cylinder/piston space through holes 454 (FIG. 15D) in the upper end of the piston.

In an embodiment of the invention, filling of the piston/cylinder space with air pushes the pneumatic piston towards the device's upper side thus transforming the device into a ring like configuration.

On the distal end of the piston 450 there is a snapping element 448, when the device reaches the ring like configuration the snapping element snaps into windows 456 in the distal end of the cylinder 452, thus keeping the device in a ring like configuration.

A removal string 458 is connected to the snapping element 448. By pulling the removal string the snapping element retracts towards a central axis of the device (FIGS. 15C-15D), releasing the piston 450 from the cylinder 452, causing the device to return to a collapsed state and allowing an easy removal of the device out of the vagina.

In some embodiments of the invention, the detachable tube 444 also functions as the removal string 458.

In an embodiment of the invention, the pump 446 is disconnected from the device after deployment.

Exemplary Locking Mechanism Embodiments

Figure 16:
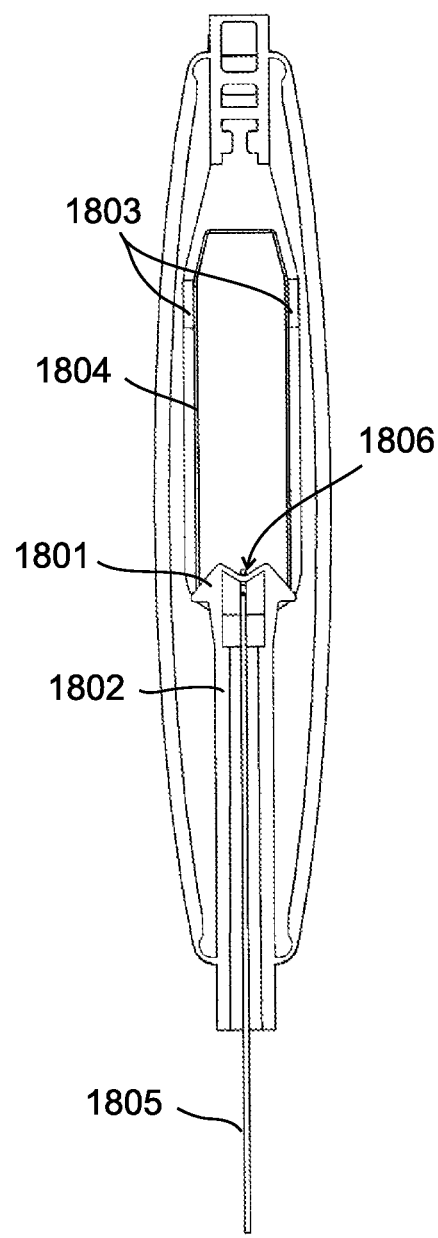
FIG. 16 is a front view of a locking mechanism with an integral snap on an inner tube, in accordance with an exemplary embodiment of the invention.

FIG. 16 is a front view of a locking mechanism 1800 including an integral snapping element 1801 on an inner tube 1802, in accordance with an exemplary embodiment of the invention. In an embodiment of the invention, the flexible integral snapping element 1801 on the inner tube is configured to snap into counterpart cut-outs 1803 on an outer tube 1804. In an embodiment of the invention, the inner tube 1802 is slidable within the outer tube 1804 and upon the application of a pushing force (pushing, optionally from an applicator, the inner tube in a distal direction) on the inner tube 1802, the locking mechanism 1800 locks the device when prongs of the snapping element 1801 pop into the cut-outs 1803, preventing the inner tube 1802 from sliding in a proximal direction within the outer tube 1804.

Figure 17:
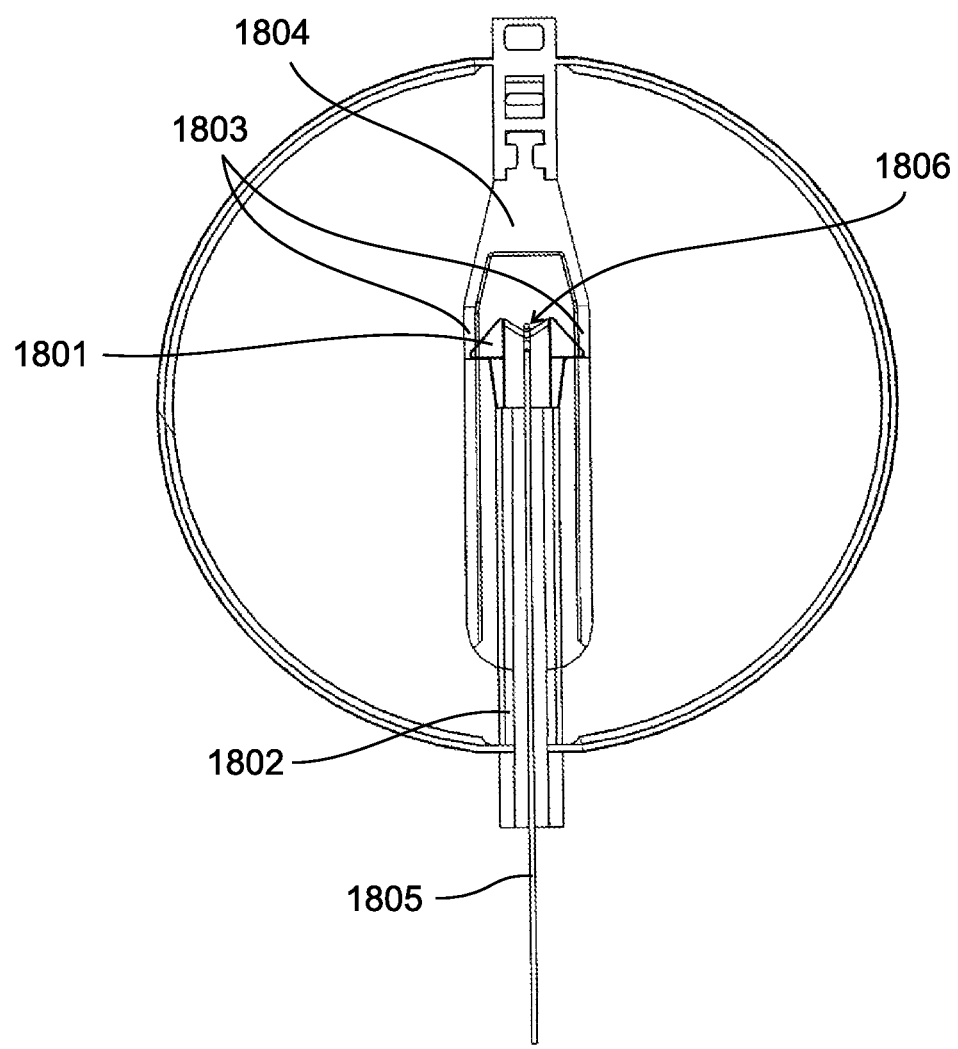
FIG. 17 is a cross-sectional view showing the locking mechanism of FIG. 16 locked, in accordance with an exemplary embodiment of the invention.
Figure 18:
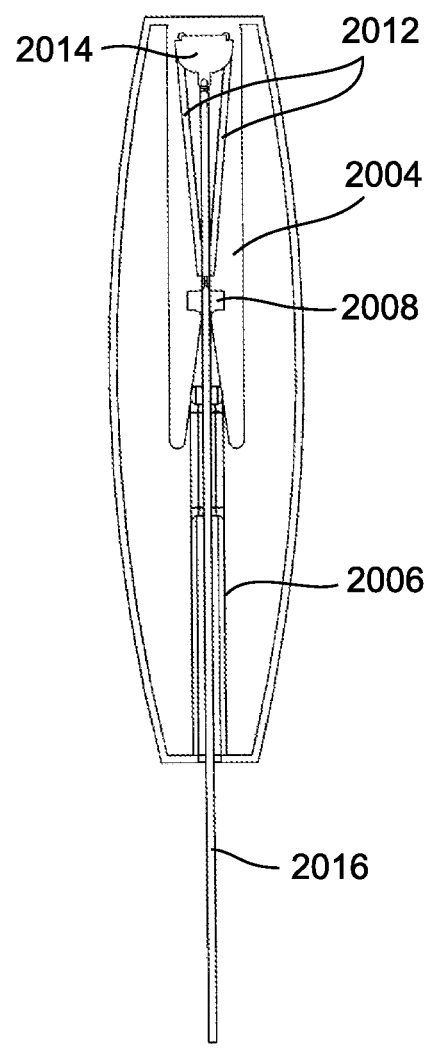
FIGS. 18-19 are front views of a locking mechanism with an axial integral snapping element, unlocked and locked respectively, in accordance with an exemplary embodiment of the invention.

FIG. 17 is a cross-sectional view showing the locking mechanism 1800 of FIG. 18 locked, in accordance with an exemplary embodiment of the invention. A removal string 1805 is connected to a bridge 1806 connecting the snaps of the snapping element 1801. In an embodiment of the invention, release of the locking mechanism 1800 is achieved by pulling the removal string 1805 in a proximal direction, causing the bridge 1806 to bend and contraction of the snapping element 1801 towards a central axis of the device, removing the snaps of the snapping element 1801 from their counterpart cut-outs 1803 and re-enabling the sliding of the inner tube 1802 within the outer tube 1804.

Figure 19:
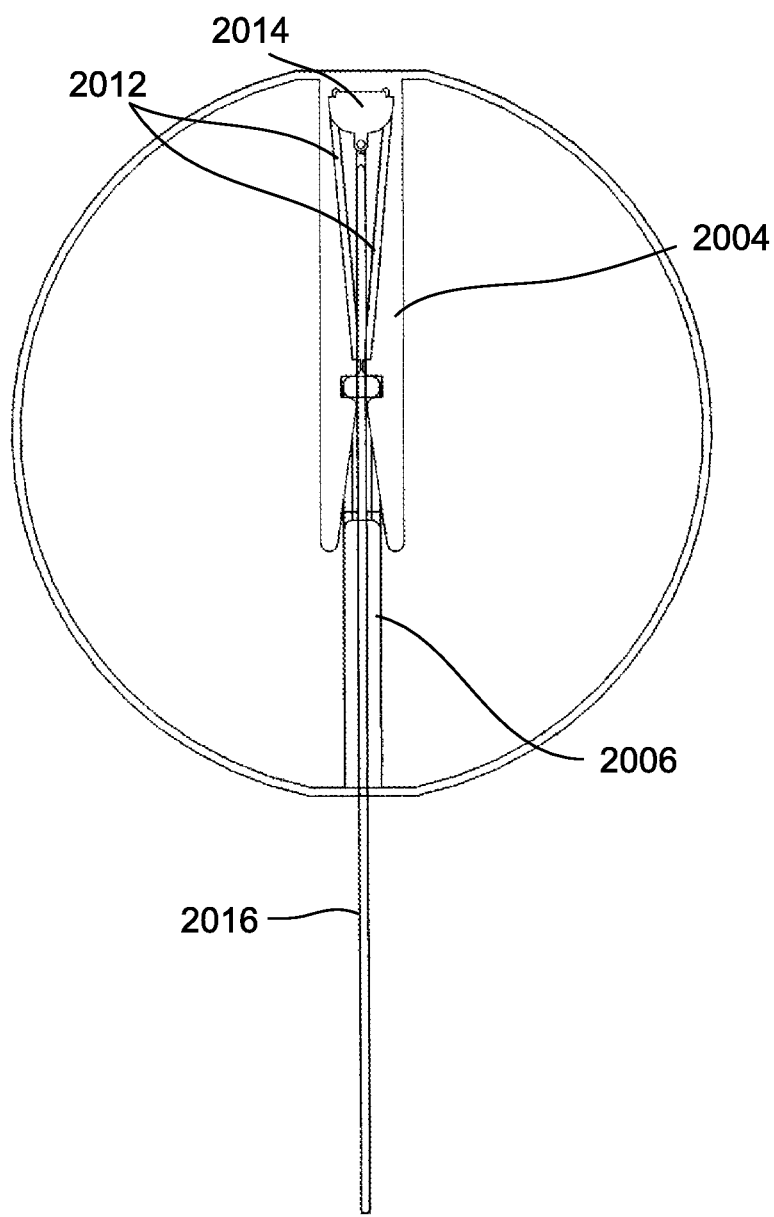

FIGS. 18-19 are front views of a locking mechanism 2000 with an axial integral snapping element, unlocked and locked respectively, in accordance with an exemplary embodiment of the invention. The upper locking element 2004 is a clip shape stud with flexible arms that are configured to snap into an opening (shown in FIG. 20) in the lower locking element 2006 and thus lock the device into an expanded state (shown in more detail in FIG. 19). In an embodiment of the invention, the lower locking element is pushed upwards in between the two flexible arms of the upper locking element 2004 bending them outwards until it latches in a trans-axial trench 2008 (shown in FIG. 18).

Figure 20:
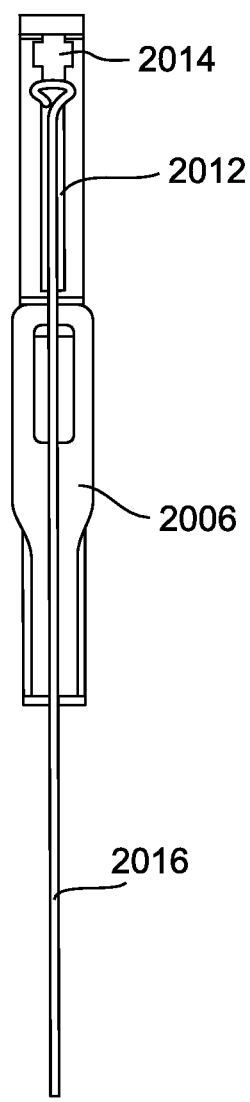
FIG. 20 is a cross-sectional perspective view of the device depicted in FIGS. 18-19 showing the locking mechanism in more detail, in accordance with an exemplary embodiment of the invention.

FIG. 20 is a detailed section side view of the device depicted in FIGS. 18-19. Axial grooves 2012 are provided in the internal side of each of the flexible arms of the upper locking element 2004 above the trans-axial trench 2008 such that an opening element 2014 (shown in more detail in FIG. 21) can slide in a proximal direction within the axial grooves 2012 upon the application of a pulling force on a removal string 2016.

Figure 21:
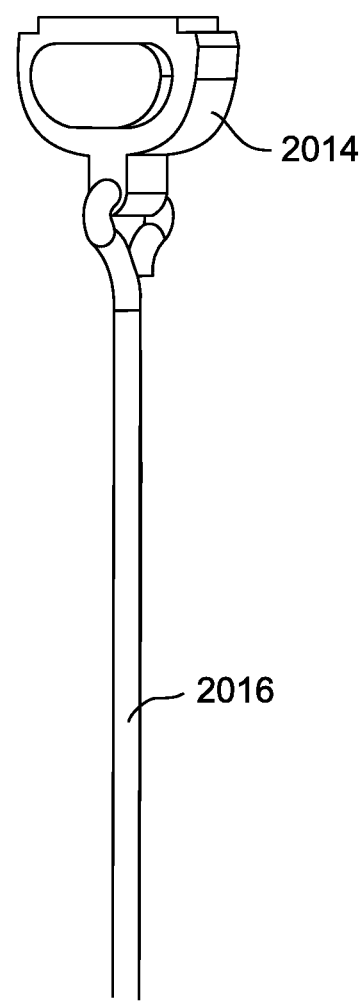
FIG. 21 is a perspective view of a removal string attached to an opening element of the locking mechanism shown in FIG. 18 or 20, in accordance with an exemplary embodiment of the invention.

FIG. 21 is a perspective view of the removal string 2016 attached to the opening element 2014 of the locking mechanism 2000 shown in FIGS. 18-20, in accordance with an exemplary embodiment of the invention. When a pulling force (in the proximal direction) is applied to the removal string 2016, the opening element 2014 slides in the axial grooves 2012 of the flexible arm of the upper locking element 2004, causing the slanted arms to gradually spread and disengage the lower locking element 2006 from the trans-axial trench 2008 of the upper locking element 2004. This releases the locking mechanism and allows the device to transform back to a collapsed state for easier removal of the device from the user's vagina.

Figure 22:
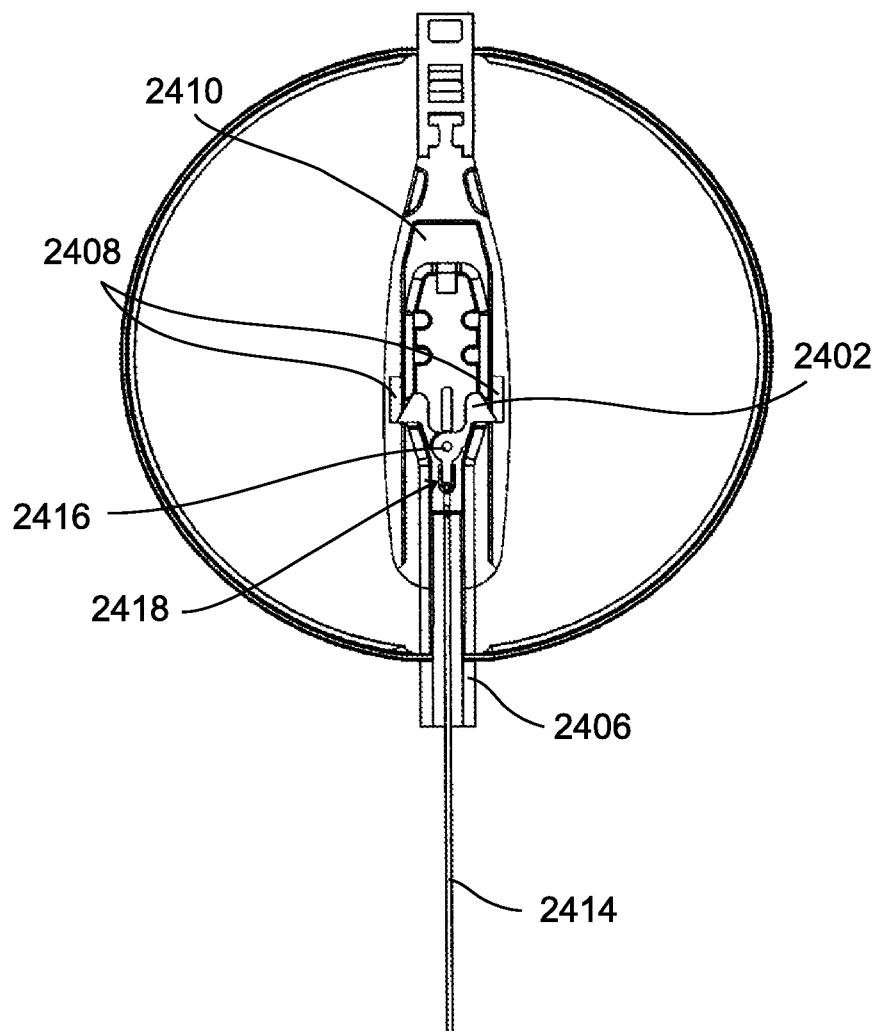
FIG. 22 is a cross-sectional view of a locking mechanism with a rotating snap in an inner tube in accordance with an exemplary embodiment of the invention.

FIG. 22 is a front view of a locking mechanism 2400 with a rotating snap 2402 in an inner tube 2406 in accordance with an exemplary embodiment of the invention. In an embodiment of the invention, the locking mechanism 2400 comprises a telescopic system that has a rotating snapping element 2402 in the inner tube 2406 that snaps into counterpart cut-outs 2408 of an outer tube 2410 when the inner tube 2406 is advanced far enough in a distal direction (optionally, upon application of pressure by an applicator) into the outer tube 2410.

Figures 23, 24:
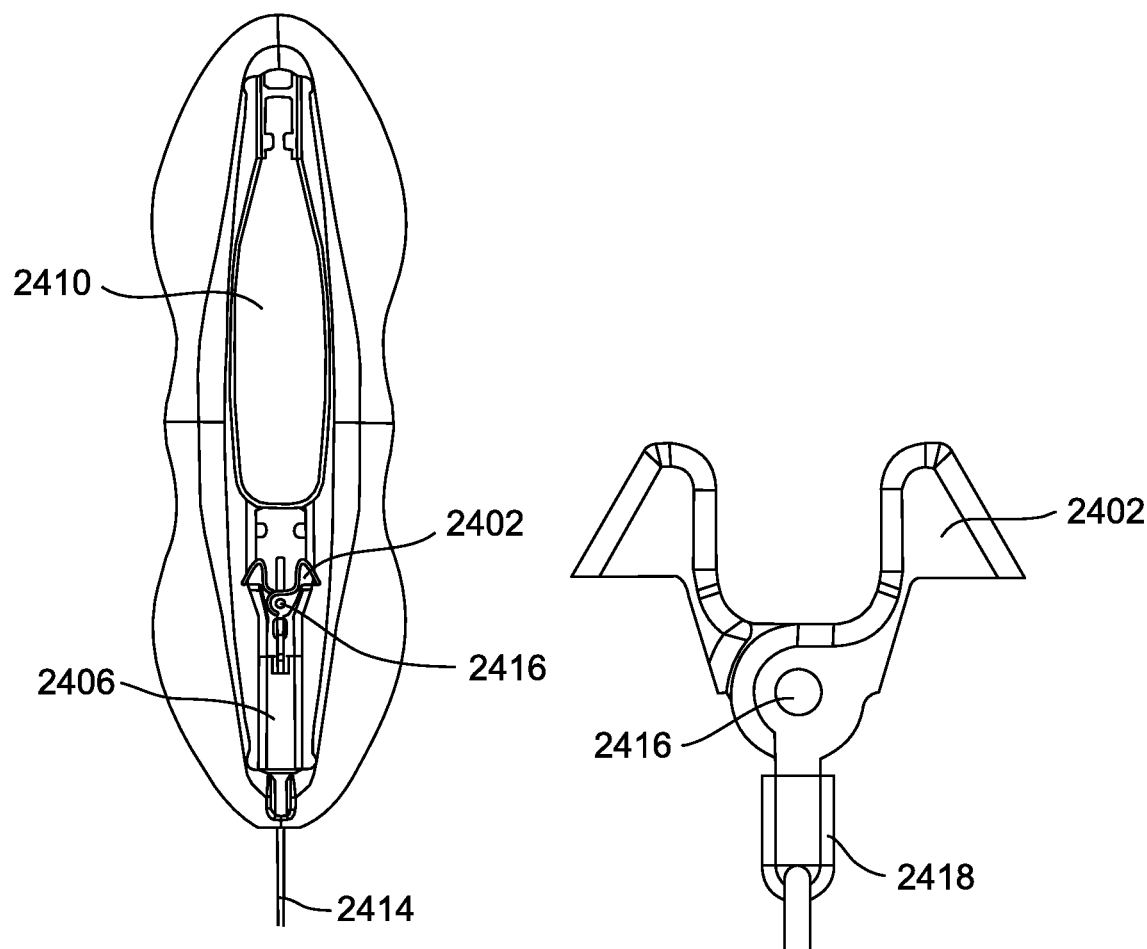
FIG. 23 is a front view of a device with a locking mechanism of FIG. 22, in accordance with an exemplary embodiment of the invention.
FIG. 24 is close-up side view of a snapping element of the locking mechanism of FIG. 22 and a removal string, in accordance with an exemplary embodiment of the invention.

FIG. 23 is a front view of a device in a compressed state with an unlocked locking mechanism 2400 of FIG. 22, in accordance with an exemplary embodiment of the invention.

FIG. 24 is close-up view of the rotating snap 2402 of the locking mechanism 2400 of FIG. 22 and a removal string 2414, in accordance with an exemplary embodiment of the invention. In some embodiments of the invention, the rotating snap 2402 is constructed of two halves, connected by an axis 2416 around which each half is rotatable. In some embodiments of the invention, the removal string 2414 is attached to the rotating snap 2402 by a holder 2418, where the holder holds together a part of each of the halves of the snap 2402.

Figure 25A:
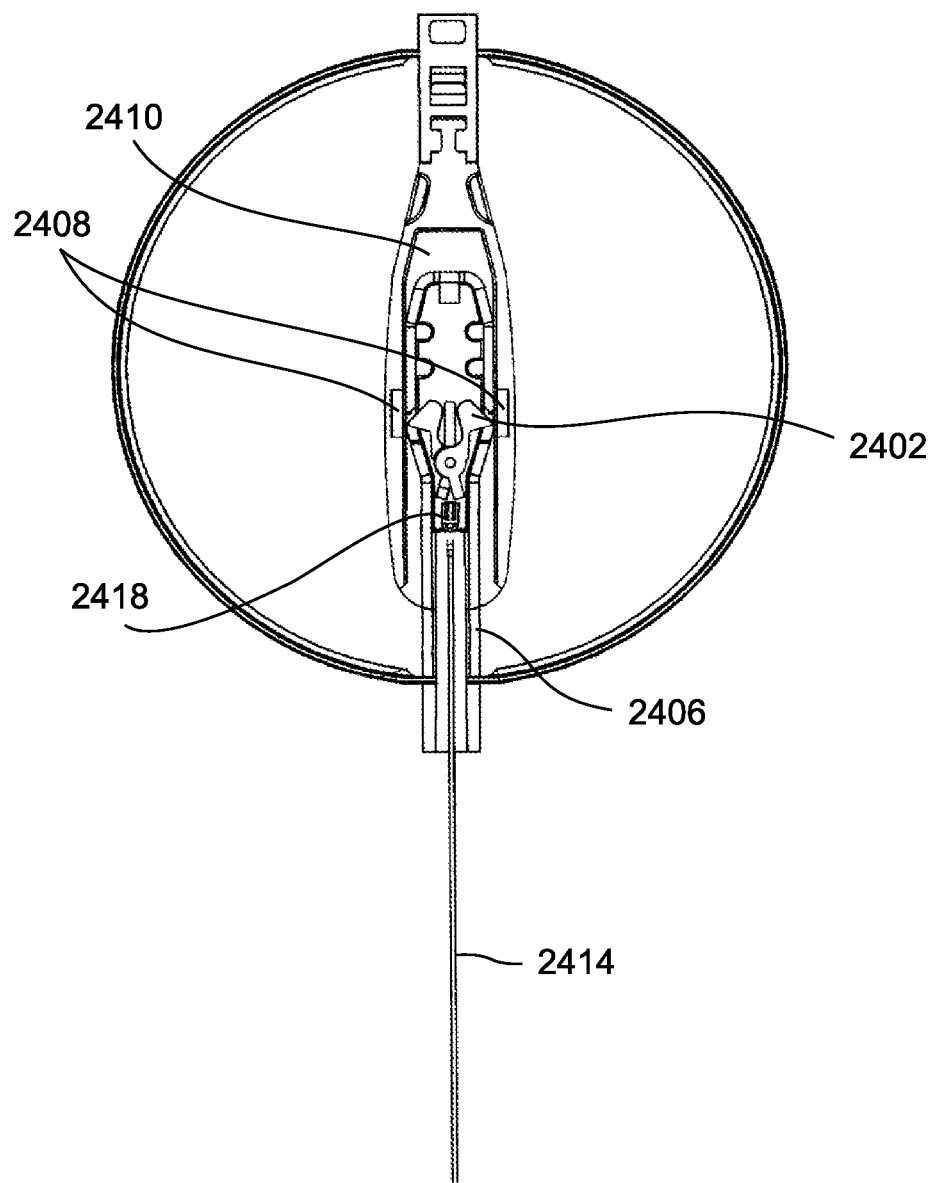
FIGS. 25A and 25B are cross-sectional views of the locking mechanism of FIG. 22 after the removal string of FIG. 24 has been pulled, in accordance with an exemplary embodiment of the invention.
Figure 25B:
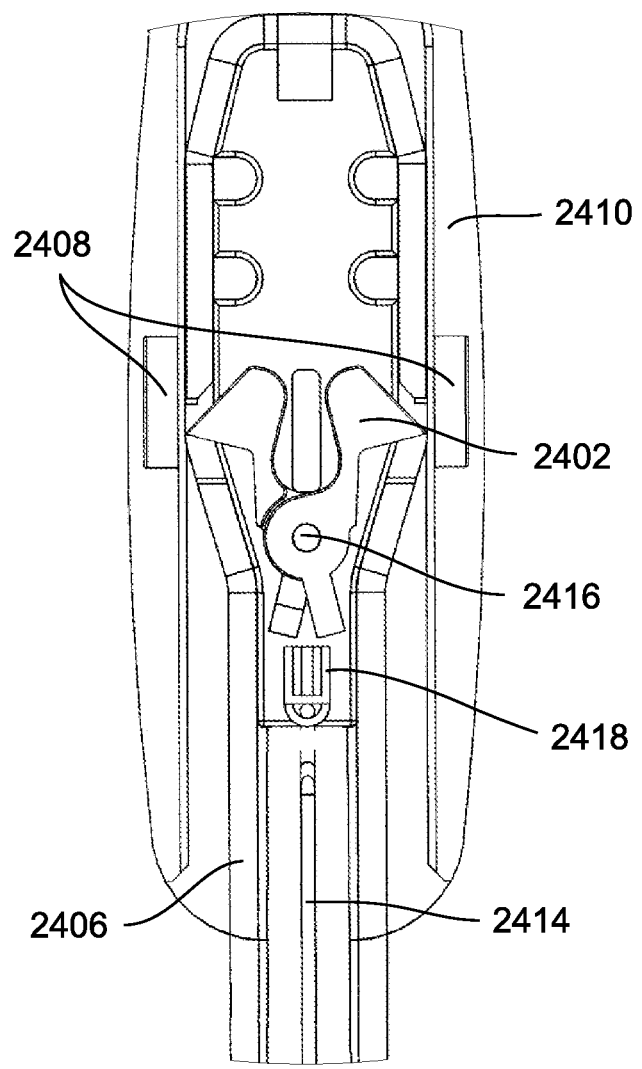

FIGS. 25A-25B are cross-sectional front views of the locking mechanism 2400 of FIG. 22 after the removal string 2414 has been pulled, in accordance with an exemplary embodiment of the invention. In an embodiment of the invention, by pulling the string 2414, the holder 2418 is detached from the rotating snap 2402. When not held by the holder 2418, the two halves of the snap are free to rotate inwards and release the snaps from the cut-outs 2408, allowing for a transition of the device to a collapsed state and for an easy removal of the device out of the user's vagina.

Exemplary Applicator Embodiments

In some embodiments of the invention, an applicator is provided to insert and/or deploy a feminine pelvic organ prolapse treating device. Applicators are optionally, specially designed to insert and/or deploy specific device embodiments, depending on factors such as device shape, locking mechanism and/or state change mechanism operation and/or device operation. In some embodiments of the invention, more general purpose applicators are provided which could be used for insertion and/or deployment of more than one device embodiment.

Figure 26:
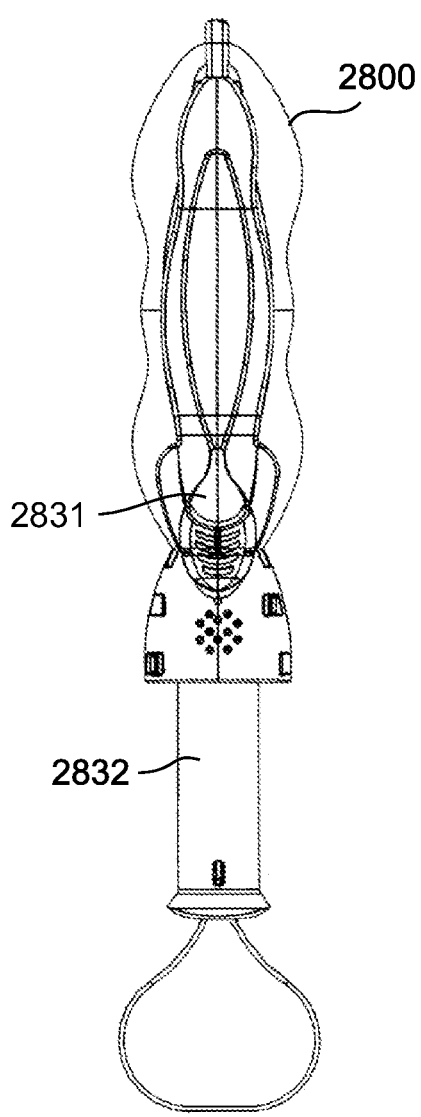
FIG. 26 is a perspective view of a closed device for treating pelvic organ prolapse attached to an externally connected arm applicator, in accordance with an exemplary embodiment of the invention.
Figure 27:
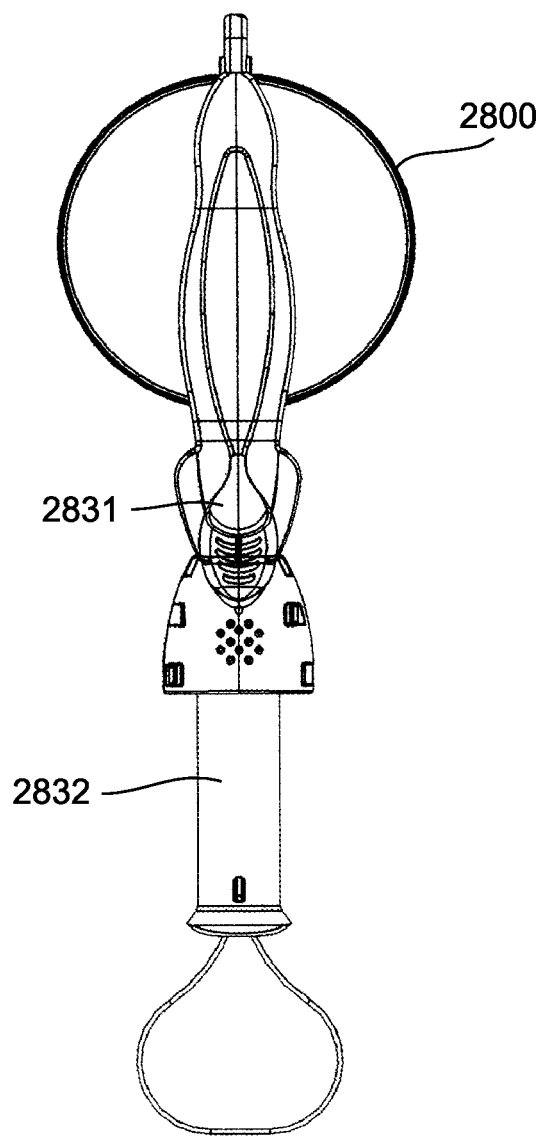
FIG. 27 is a perspective view of the applicator of FIG. 26 deploying the device of FIG. 26, in accordance with an exemplary embodiment of the invention.

FIG. 26 is a front view of a closed device 2800 for treating pelvic organ prolapse attached to an externally connected arm applicator 2830, in accordance with an exemplary embodiment of the invention. In an embodiment of the invention, the applicator 2830 is attached to the device 2800 and is used for insertion and/or deployment (switching the device to the expanded state) of the device into a vagina. In an embodiment of the invention, the applicator 2830 comprises at least two components: a holder 2831 and pusher 2832. In an embodiment of the invention, the holder 2831 and the pusher 2832 are assembled in a way that allows axial movement of the pusher relative to (and inside of) the holder such that exerted force on the pusher in a distal direction will push the device into a locked, expanded state (such as shown in FIG. 27).

Figure 28:
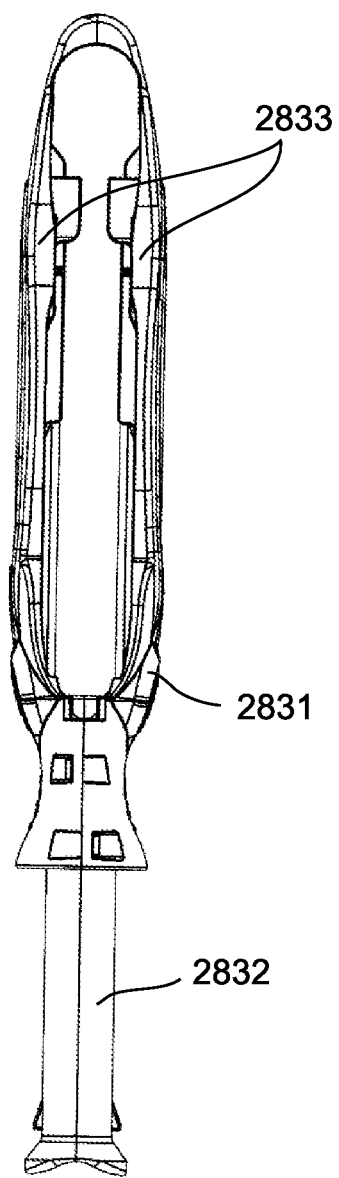
FIG. 28 is a side view of the applicator of FIG. 26, in accordance with an exemplary embodiment of the invention.

FIG. 28 is a front view of an externally connected arm applicator 2830, in an embodiment of the invention, the holder 2831 is comprised of two opposing arms 2833. In the initial, insertion configuration, the pusher 2832 is pulled backward/downward (proximally) and the device 2800 is encased by the two holder arms and held in its unexpanded state. When the pusher 2832 moves in a distal direction within the holder 2831 it presses the device 2800 and gradually transfers the device from its stick like configuration to the ring like configuration—expanded position. When reaching the ring like configuration, the device is locked by an internal locking mechanism.

Figure 29:
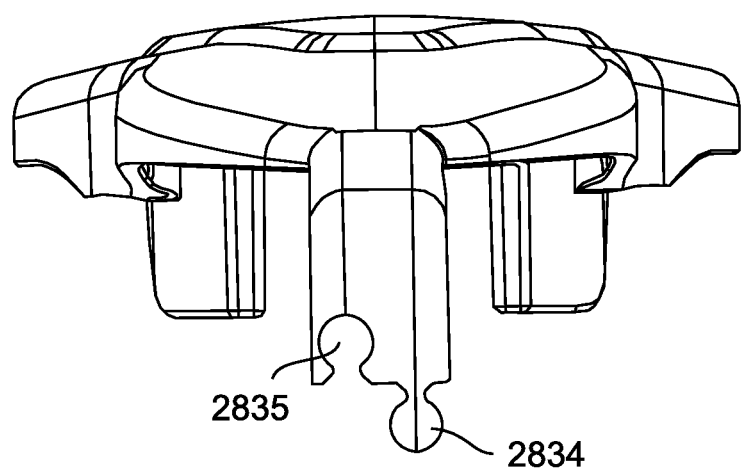
FIG. 29 is a top view of one arm of the applicator of FIG. 26, in accordance with an exemplary embodiment of the invention.

FIG. 29 is a top view of an externally connected arm applicator 2830, in an embodiment of the invention, the holder arms 2833 are releasably held together by a protruding snap element 2834 attached to an opposite opening 2835 designed to close the far/distal end of the applicator 2830 thus encasing and holding the device 2800.

Figure 30:
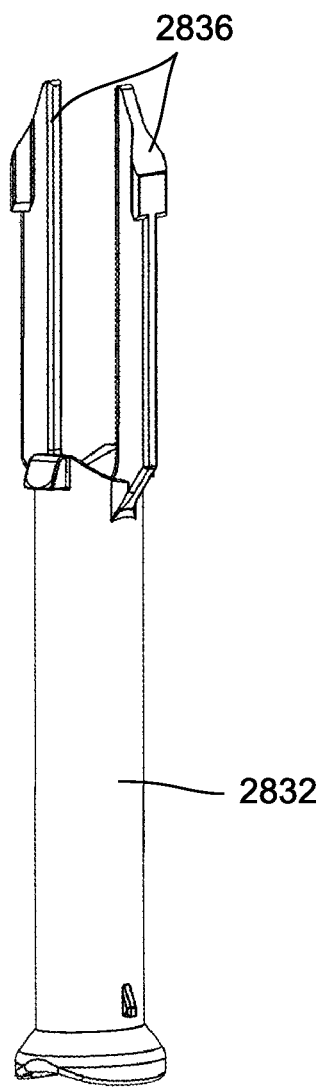
FIG. 30 is a perspective view of the pusher of the applicator of FIG. 26, in accordance with an exemplary embodiment of the invention.

FIG. 30 is a prospective view of the pusher 2832, in an embodiment of the invention, the pusher 2832 has two or more protruding arms 2836. After the device 2800 reaches the expanded state, additional distal movement of the pusher 2832 brings the pusher's arms 2836 in contact with the holder arms 2833, exerting a separation pressure on the arms and causing the snap elements 2834/2835 to unsnap, enabling detachment of the device from the holder 2831. The applicator 2830 is then pulled proximally/downwards, out of the vagina, while the device 2800 is left inside.

Figure 31:
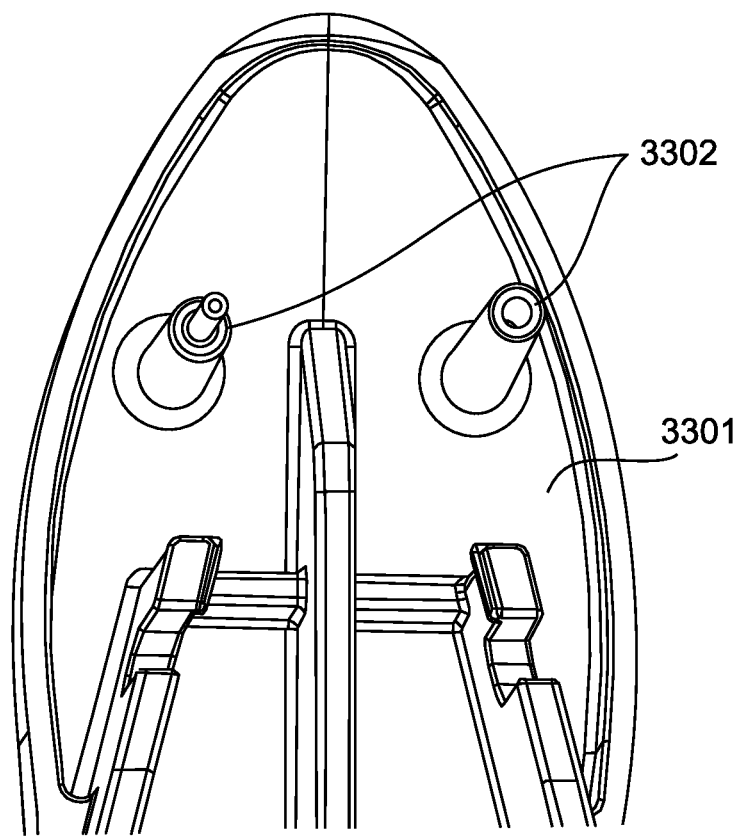
FIG. 31 is a close-up perspective view of the end of one arm of an applicator holder, in accordance with an exemplary embodiment of the invention.

FIG. 31 is close-up perspective view of the end of one arm 3301 of an applicator holder, which instead of having arms connected by a snap element (like the embodiments described in FIGS. 26-29), has arms reversibly connected by protruding concentric pillars 3302, in accordance with an exemplary embodiment of the invention. Insertion and/or device deployment operations are otherwise substantially similar to those of the embodiment described in FIGS. 26-29.

Figure 32:
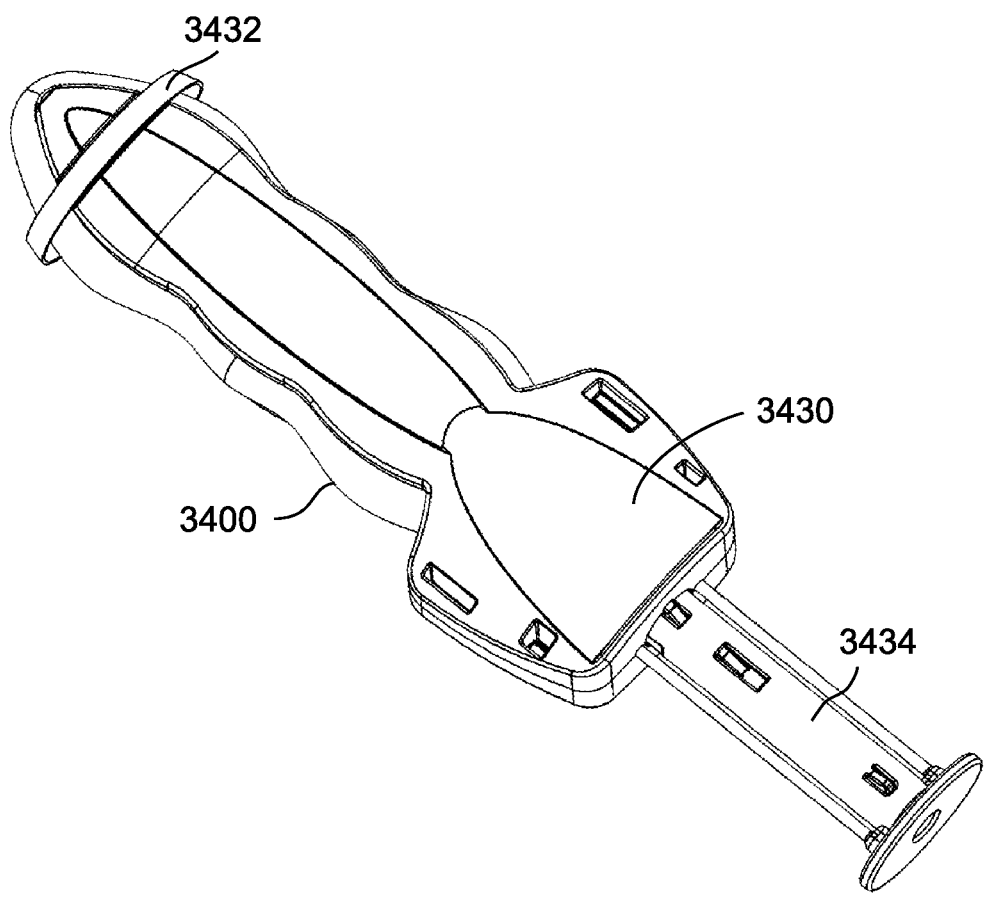
FIG. 32 is a perspective view of a device for treating prolapse with a band/strap applicator, in accordance with an exemplary embodiment of the invention.

FIG. 32 is a perspective view of a device 3400 for treating prolapse with a band/strap applicator 3430, in accordance with an exemplary embodiment of the invention. General construction and operation of the applicator 3430 is similar to other embodiments described herein, with a difference being that the arms of the holder are reversibly held together by a band/strap 3432, instead of a snapping element or concentric pillars, as examples. In an embodiment of the invention, the band/strap 3432 keeps the arms of the applicator 3430 closed so that the device 3400 cannot detach from it. In an embodiment of the invention, the band 3432 is released/broken during deployment of the device 3400 as a result of the expansion pressure exerted on the device 3400 from the pusher 3434 of the applicator. In an embodiment of the invention, the band 3432 is attached to the applicator 3430 such that even after it is released it will be withdrawn from the vagina when the applicator 3430 is pulled out.

Figure 33:
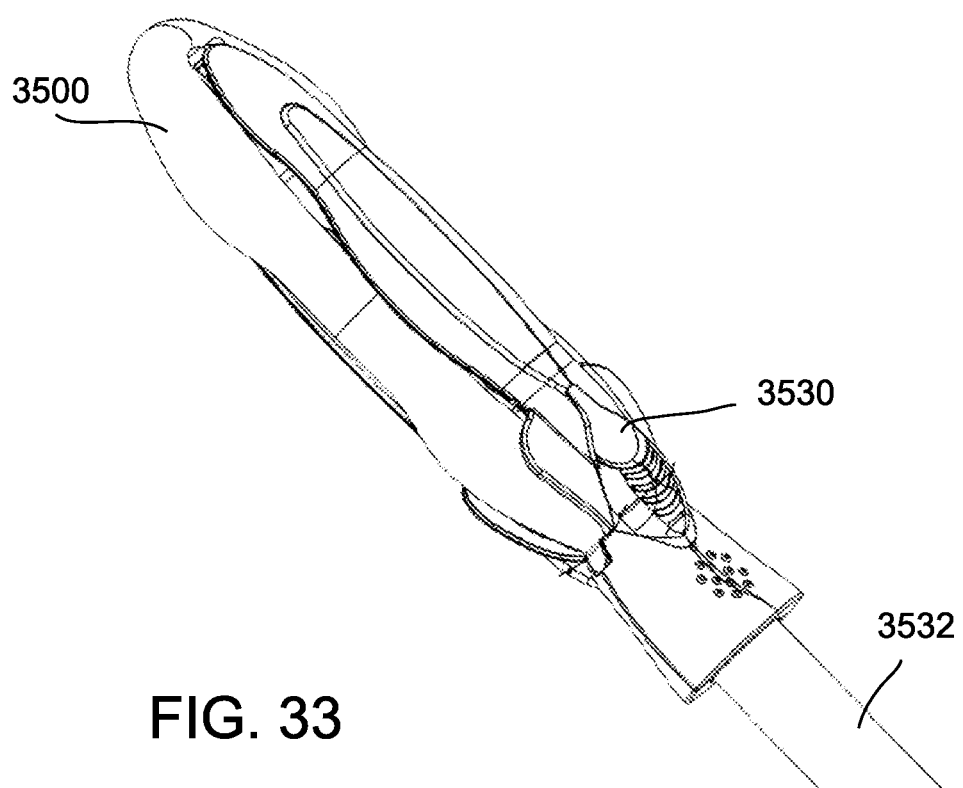
FIGS. 33 and 34 are perspective views of a device for treating prolapse with a rail applicator, in accordance with an exemplary embodiment of the invention.
Figure 34:
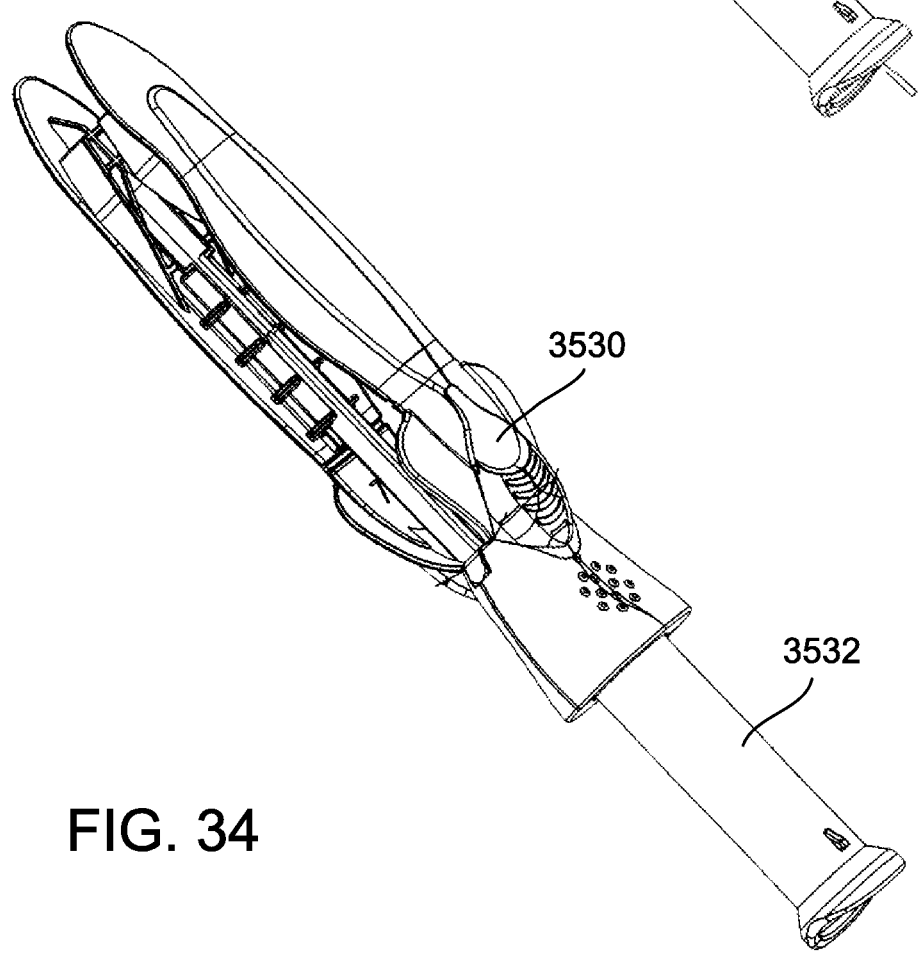

FIG. 33 is a perspective view of a device 3500 for treating prolapse with a rail applicator 3530 (FIG. 34), in accordance with an exemplary embodiment of the invention. General construction and operation of the applicator 3530 is similar to other embodiments described herein.

Figure 35:
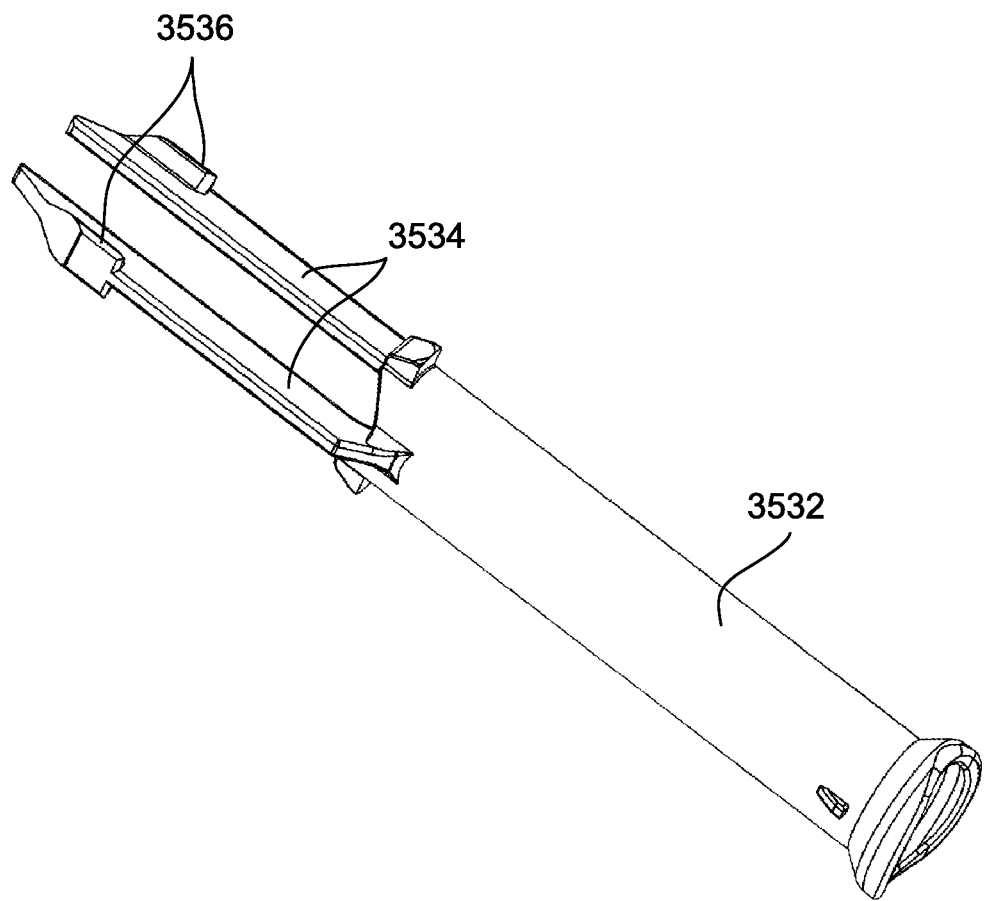
FIG. 35 is a perspective view of the rail applicator pusher of FIGS. 33-34, in accordance with an exemplary embodiment of the invention.
Figure 36:
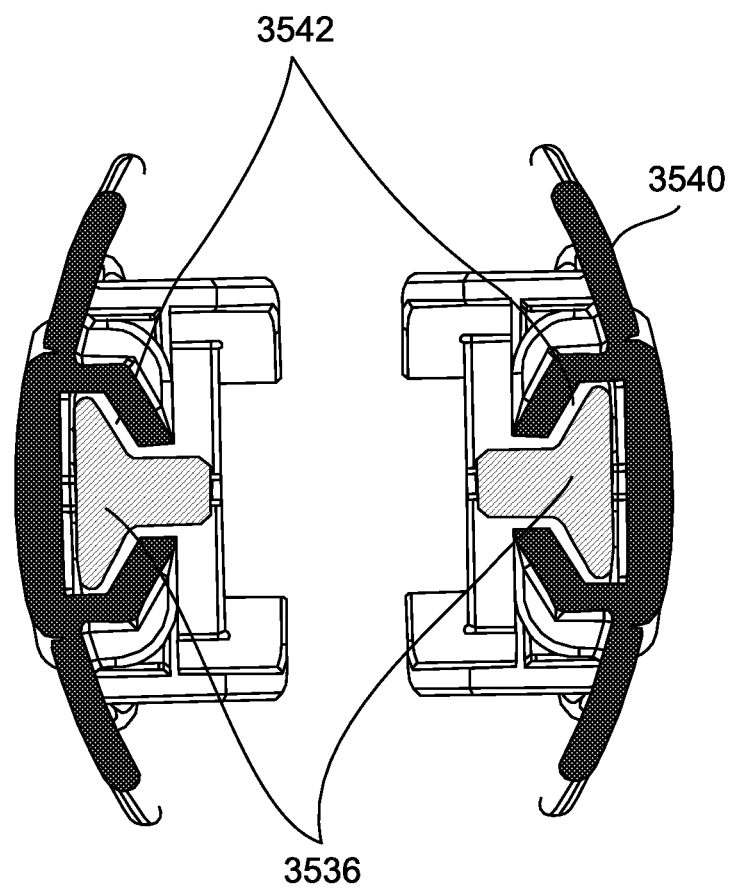
FIG. 36 is a cross-sectional view of the applicator of FIGS. 33-34, in accordance with an exemplary embodiment of the invention.

FIG. 35 is a perspective view of a rail applicator pusher 3532 having arms 3534 with widen upper tips 3536. The widen tips slide within rails 3542 (shown in the cross-sectional view FIG. 36) inside the applicator holder arms 3540. The shape of the pusher arms 3534 are configured in conjunction with the rail 3542 of the holder such that the pusher maintains the holder closed (and the device 3500 trapped therein) as the pusher slides in a distal direction along the holder until the pusher arms 3534 reach an opening in the holder rail, release the holder arms from the pusher and allow the holder arms to bend outwards and release the hold on the device 3500. The location of the opening in the holder rail is configured to coincide with travel required for the device 3500 to fully transform to the expanded state and/or be locked into the expanded state by a locking mechanism.

After the device is device is expanded and released from the applicator, the applicator 3530 is withdrawn.

Exemplary Additional Embodiments

Figure 37A:
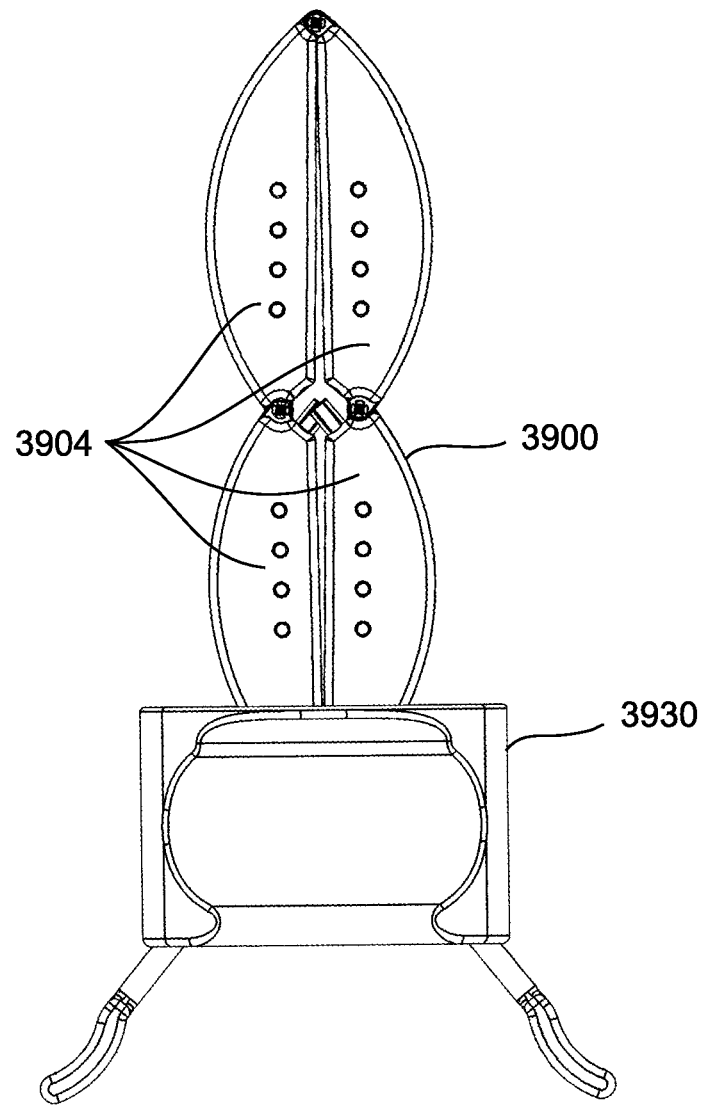
FIG. 37A is a perspective view of a rhombus shaped device configured for treating pelvic organ prolapse with an applicator, in accordance with an exemplary embodiment of the invention.

FIG. 37A is a perspective view of a hinge activated device 3900 configured for treating pelvic organ prolapse with an applicator 3930 with an optional elastomeric cap 3902 (not shown in the figures), in accordance with an exemplary embodiment of the invention. In some embodiments of the invention, the elastomeric cap 3902 is used for at least one of protecting the device 3900 from body fluids and debris; avoiding vaginal wall pinching by the device (during insertion/expansion); and, adding extra side pressure to ensure device complete transformation to the compressed state prior to removal.

Figure 37B:
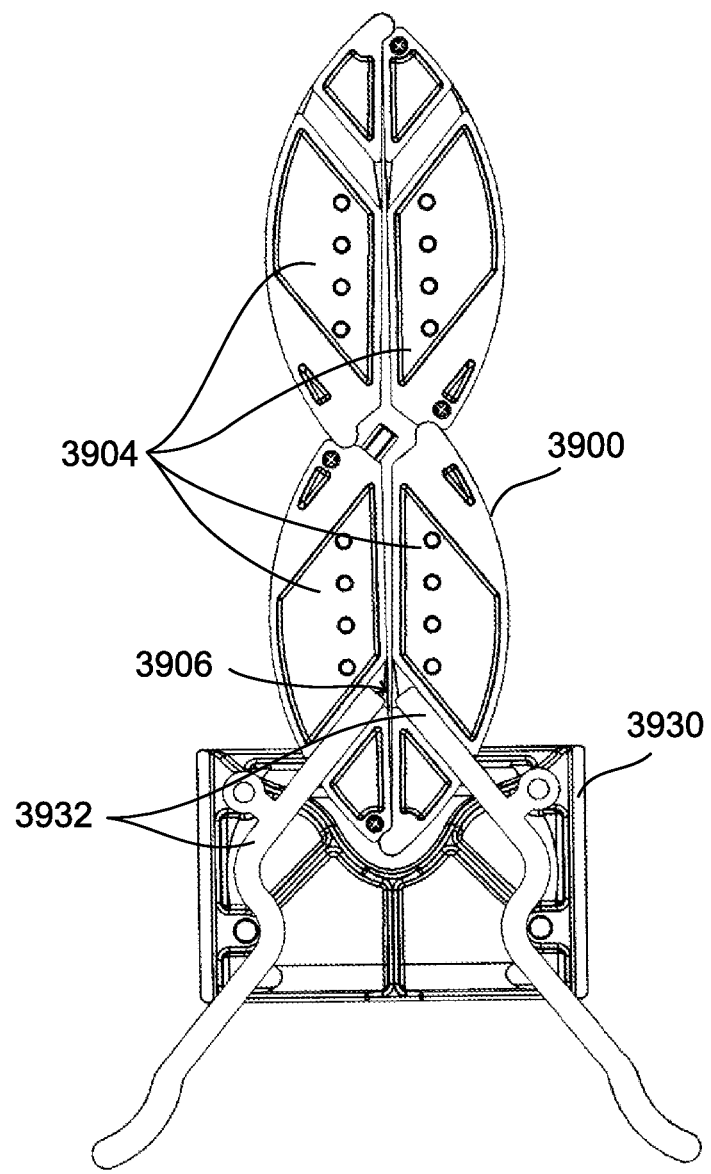
FIG. 37B is a cross-sectional view of the rhombus shaped device and applicator of FIG. 37A, in accordance with an exemplary embodiment of the invention.

FIG. 37B is a cross-sectional view of the hinge activated device 3900 and applicator 3930 of FIG. 37A, in accordance with an exemplary embodiment of the invention. In an embodiment of the invention, the device 3900 is constructed of 4 shaped sections 3904 which when expanded have a circular shape, but when collapsed have a narrow, vaguely figure-8 shape. When expanded, the device 3900 has a rhomboid internal space (shown in FIG. 39). In some embodiments of the invention, the sections 3904 have cuts 3906 which are adapted for receipt of applicator arms 3932. In some embodiments of the invention, the sections 3904 have cuts 3908 which are adapted for receipt of spring locks 3912.

Figure 38A:
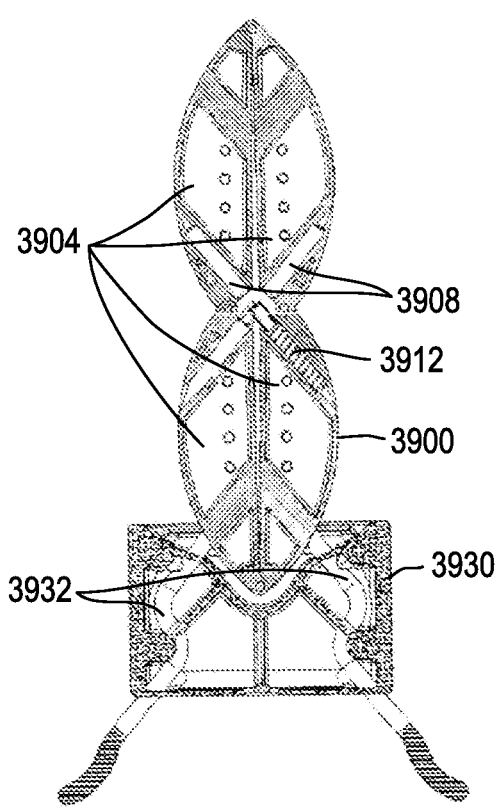
FIGS. 38A-38C are sequential perspective views showing the applicator deploying the device of FIGS. 37A and 37B, in accordance with an exemplary embodiment of the invention.
Figure 38B:
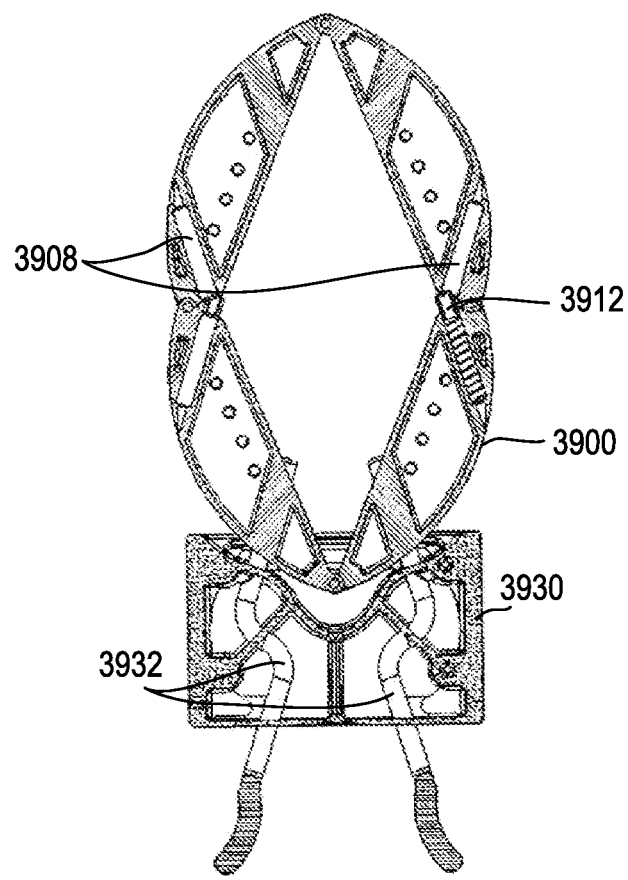
Figure 38C:
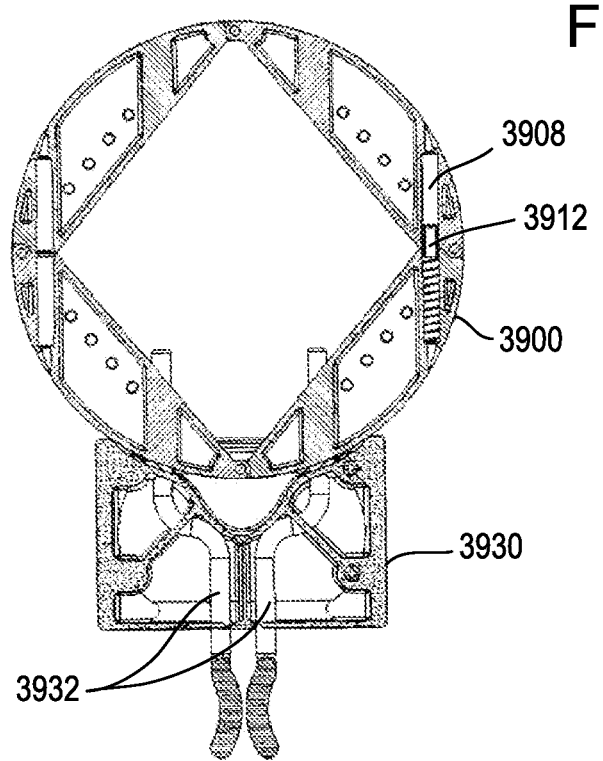

FIGS. 38A-38C are sequential perspective views showing the applicator 3930 deploying the device 3900 of FIGS. 37A and 37B, in accordance with an exemplary embodiment of the invention. Pressing the two applicator arms 3932 towards each other forces the device 3900 to transfer from the figure-8, compressed configuration to the circular, expanded configuration as the rotation of the hinges and the shapes of the sections force the device to assume the circular expanded form. When reaching the ring like configuration, the device is locked by the spring locks 3912 which pop into the aligned cuts 3908 located opposite the spring locks 3912 in the opposite sections 3904. The spring locks 3912 are kept uncompressed during storage and undergo compression only for a short period during the configuration transformation when the spring lock heads encounter the adjacent section 3904 surfaces (see FIG. 38B).

In the initial applicator/device configuration (shown in FIG. 38A) the applicator arms 3932 are angled towards each other while inside their respective cuts 3906, thus the applicator 3930 cannot detach from the device 3900. When the device 3900 is in the expanded configuration (locked device—FIG. 38C) the applicator arms 3932 are parallel and the applicator 3930 can be removed by pulling it away from the device 3900 (leaving the locked device inside the vagina).

Figure 39:
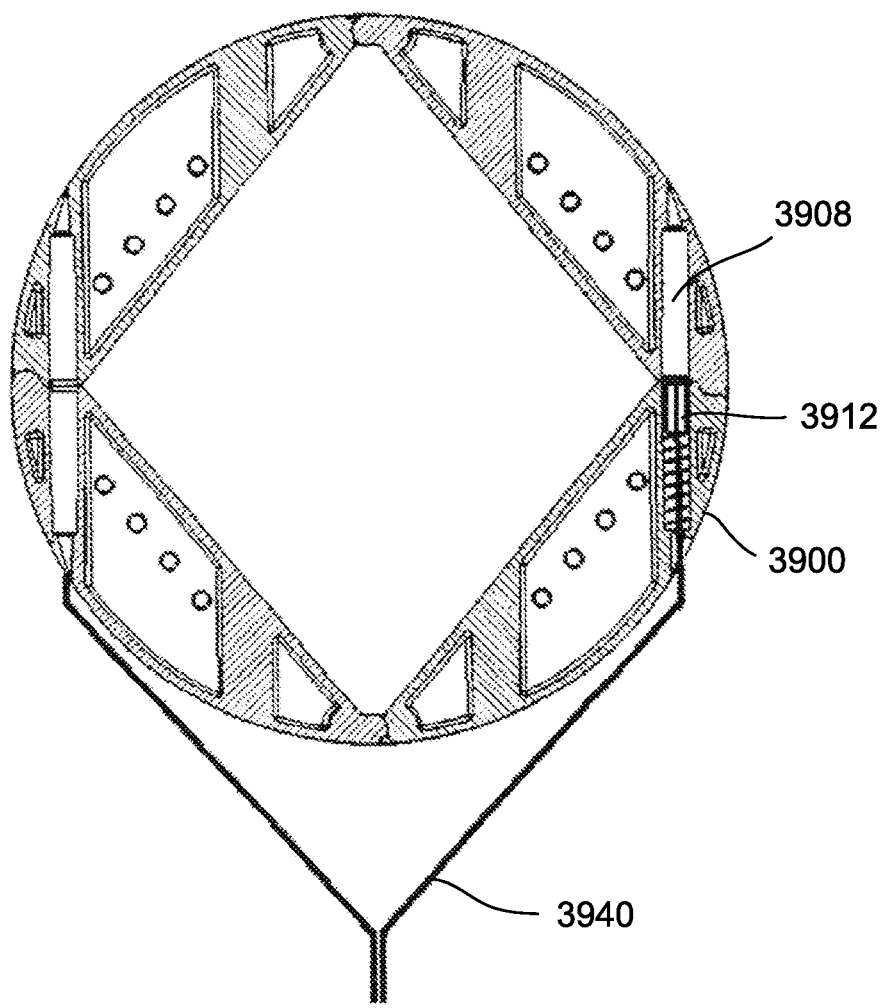
FIG. 39 is a cross section view of a rhombus shaped device in its expanded state configured for treating pelvic organ prolapse with a removal string being pulled to collapse the device for removal, in accordance with an exemplary embodiment of the invention.

FIG. 39 is the hinge activated device 3900 of FIGS. 38A-38C with a removal string 3940 being pulled to collapse the device 3900 for removal, in accordance with an exemplary embodiment of the invention. In an embodiment of the invention, the removal string 3940 is connected to each of the spring locks 3912. By pulling the removal string 3940 the spring locks are retracted, the lock is released and the device can be transitioned back to a compressed state for removal of out of the vagina.

Figure 40:
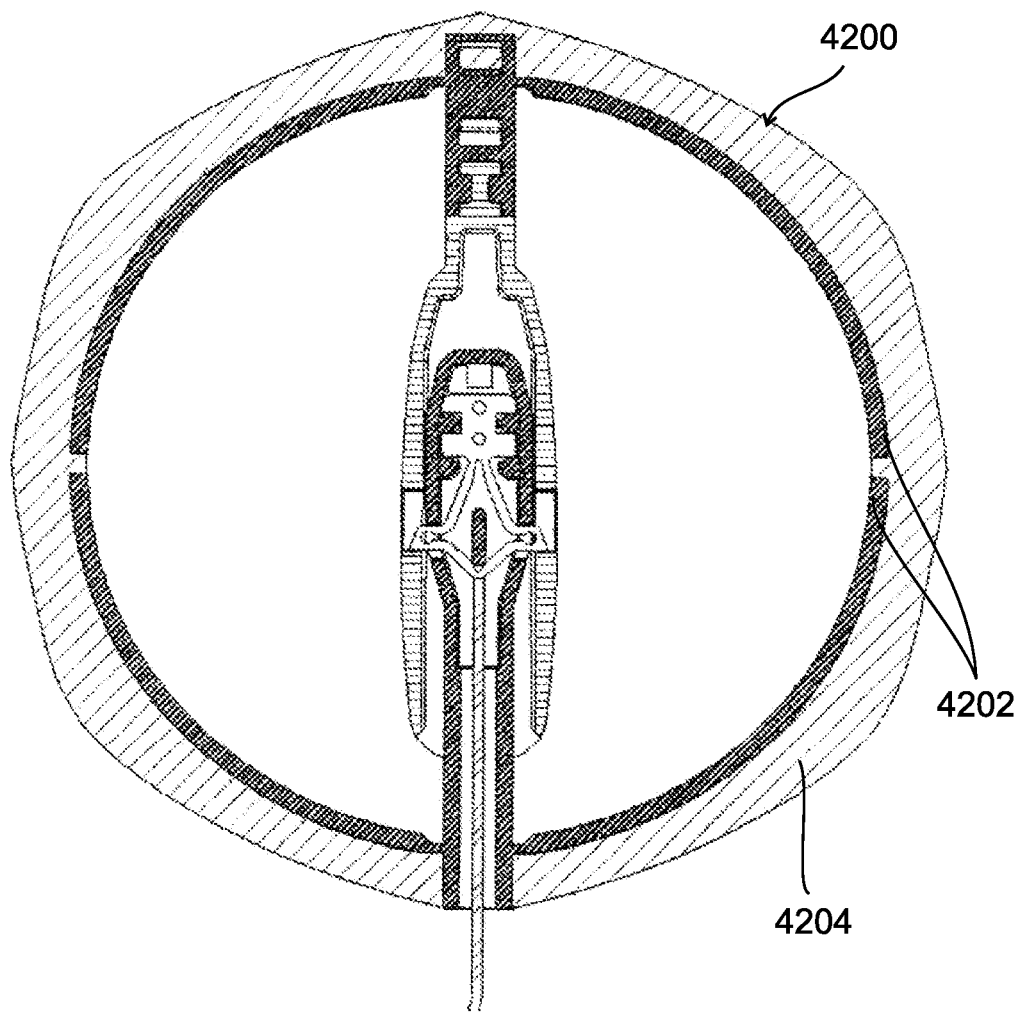
FIG. 40 is a cross sectional view of a prolapse treating device with a non-continuous ring, in accordance with an exemplary embodiment of the invention.

FIG. 40 is a cross sectional view of a prolapse treating device 4200 with a non-continuous ring 4202, in accordance with an exemplary embodiment of the invention. General construction and operation of the device 4200 is similar to other embodiments described herein, with a difference being that the device 4200 does not have a continuous ring but is instead a partial ring 4202 connected by a cover 4204. In an embodiment of the invention, to reduce insertion forces required, some reduction in the arc of the plastic ring (optionally constructed of HDPE) is used (from 1-180 degrees on each side) while the cover maintains the substantially ring shape of the device. It should be understood that device 4200 is merely an example of a discontinuous ring and that other configurations of discontinuous rings could be used. In an embodiment of the invention, the discontinuous ring configuration is used to reduce the force necessary to deploy/expand the device in situ.

Figure 41:
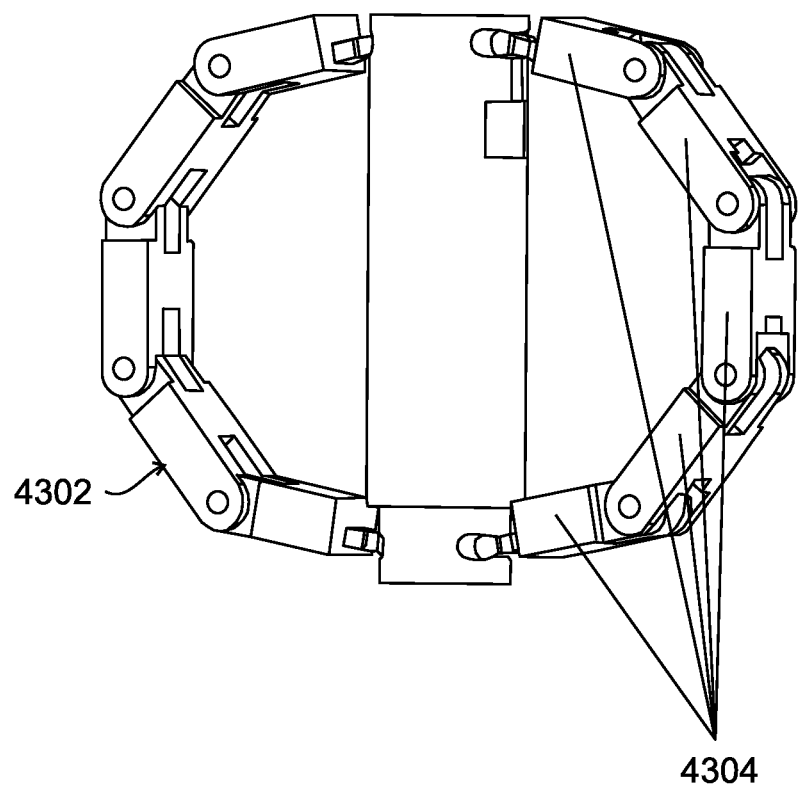
FIG. 41 is a perspective view of a prolapse treating device with a multi-link structured ring, in accordance with an exemplary embodiment of the invention.

FIG. 41 is a prospective view of a prolapse treating device 4300 with chain arcs ring 4302, in accordance with an exemplary embodiment of the invention. Each vertebra 4304 of the chain arc is connected by a hinge to the next vertebra allowing the chain to transfer from a lined form to a semicircular form. The vertebra structure contain stopper element to prevent further movement after reaching the semicircular form. The chain may be covered by an over-molded elastomer or wrapped by an elastomer sleeve.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A device sized and shaped for alleviating organ prolapse when inserted into a vagina, comprising:
   (a) an adjustably flexible, planar ring;
   (b) a telescoping locking mechanism extending in a central axis of the ring, but within a plane defined by the planar ring, from a proximal side of the ring to a second side of the ring, comprising:
      (i) a first element extending from the proximal side of the ring and terminating at a distal end formed with a hollow therein, the first element including an elastic diamond shaped snap comprising an anchoring portion, the anchoring portion disposed distally from the elastic diamond shaped snap, the anchoring portion engaged in an interior of the hollow of the distal end of the first element for securing the elastic diamond shaped snap to the first element, wherein the anchoring portion is entirely encapsulated by the distal end of the first element when disposed within the hollow; and
      (ii) a second element extending from the second side of the ring, opposite the first element, including at least one window configured as a counterpart to the snap, wherein the first element is configured to slide axially within the second element such that when the snap is opposite the at least one window, the snap is released into the at least one window reversibly preventing further axial movement of the first element relative to the second element such that the device is configured to be in a locked, expanded, treatment rendering state when the snap is released into the at least one window and a reduced profile state when the snap is not in the at least one window.

2. A device according to claim 1, further comprising an applicator configured to insert into and deploy the device in the vagina, comprising:
   (a) a holder with at least two grooves configured to hold the device where the at least two grooves are penetrated by two counterpart mounds on the device; and
   (b) a pusher configured to move axially within the holder and to press the device being held in the holder from the reduced profile state into the expanded state, and to push wings of the applicator aside in order to disengage the device.

3. An applicator according to claim 2, where the holder is provided with diagonal walls which slope up moving towards the second side of the device and where the pusher is configured with two protruding arms with sloped edges which force the holder open to release the at least two grooves of the holder from the mounds of the device as the pusher is pushed in a distal direction and the sloped edges of the arms force against the diagonal walls of the holder.

4. An applicator according to claim 3, where the holder and pusher are configured to force the holder open distally of where the device is pressed into the expanded state by the pusher.

5. An applicator according to claim 2, where the holder is configured with a gripping area to facilitate a gripping of the applicator by the user and where the gripping area is configured with a soft grip for enhanced user comfort.

6. An applicator according to claim 5, where the gripping area is positioned to ensure proper depth of insertion.

7. An applicator according to claim 2, further comprising a locking mechanism which locks the pusher into the holder.

8. A device according to claim 1, further comprising a padded cover around at least a portion of the ring.

9. A device according to claim 8, where the ring is discontinuous, connected by the cover.

10. A device according to claim 1, further comprising a removal string attached to the first element and configured to contract the diamond shaped snap towards the central axis of the ring, removing the snap from the at least one window, upon an application of a proximal force on the removal string.

11. A device according to claim 1, where the ring is rigid in the locked, expanded state and where the ring is flexible when not in the expanded state.

12. A device according to claim 1, where the elastic diamond shaped snap comprises at least two opposing prongs and the at least one window consists of two windows as counterparts for the prongs.

13. A device according to claim 1, where the device is configured to be bi-stable, stable in both the expanded state and the reduced profile state.

14. A device according to claim 1, where the locking mechanism is configured to extend sufficiently from one side of the ring to another side of the ring to inhibit organ prolapse through a center of the ring.

* * * * *